(12) United States Patent
Haas

(10) Patent No.: US 9,005,247 B2
(45) Date of Patent: Apr. 14, 2015

(54) SURGICAL APPARATUS

(75) Inventor: Alexander Haas, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 376 days.

(21) Appl. No.: 13/558,724

(22) Filed: Jul. 26, 2012

(65) Prior Publication Data

US 2013/0023934 A1 Jan. 24, 2013

Related U.S. Application Data

(63) Continuation of application No. PCT/EP2010/070361, filed on Dec. 21, 2010.

(30) Foreign Application Priority Data

Jan. 27, 2010 (DE) .......................... 10 2010 000 230

(51) Int. Cl.
*A61B 17/70* (2006.01)
*A61B 17/00* (2006.01)
*A61B 19/00* (2006.01)

(52) U.S. Cl.
CPC ..... *A61B 17/7065* (2013.01); *A61B 2017/0023* (2013.01); *A61B 2019/461* (2013.01); *A61B 2019/464* (2013.01)

(58) Field of Classification Search
USPC .............................. 606/248, 249, 90, 99, 86 A
See application file for complete search history.

(56) References Cited

U.S. PATENT DOCUMENTS

| 3,648,691 | A | 3/1972 | Lumb et al. |
| 5,351,792 | A | 10/1994 | Cohen |
| 5,645,589 | A | 7/1997 | Li |
| 6,214,050 | B1 | 4/2001 | Huene |
| 6,322,883 | B1 | 11/2001 | Williams |
| 6,332,883 | B1 | 12/2001 | Zucherman et al. |

(Continued)

FOREIGN PATENT DOCUMENTS

| DE | 4411974 A1 | 10/1995 |
| DE | 69431348 T2 | 5/2003 |

(Continued)

OTHER PUBLICATIONS

Search Report for German Application No. 10 2010 000 230 .5 Dated Sep. 21, 2010.

(Continued)

*Primary Examiner* — Jerry Cumberledge
(74) *Attorney, Agent, or Firm* — RatnerPrestia

(57) ABSTRACT

A surgical apparatus includes an implant for mutually supporting an upper spinous process of a first vertebral body and a lower spinous process of a second vertebral body. The implant comprises a first implant component and a second implant component movable relative thereto along a clamping direction to transfer the implant out of a basic position in a spreading direction that is oriented transversely relative to the clamping direction into a spread position. The implant includes at least one introduction-side upper supporting element and at least one introduction-side lower supporting element that for laterally supporting the upper spinous process or the lower spinous process on the introduction-side. A fixing device for the implant is used for spreading the at least one introduction-side upper supporting element and the at least one introduction-side lower supporting element relative to each other along the spreading direction in an introduction position of the implant.

25 Claims, 23 Drawing Sheets

(56) References Cited

U.S. PATENT DOCUMENTS

Figure 1:
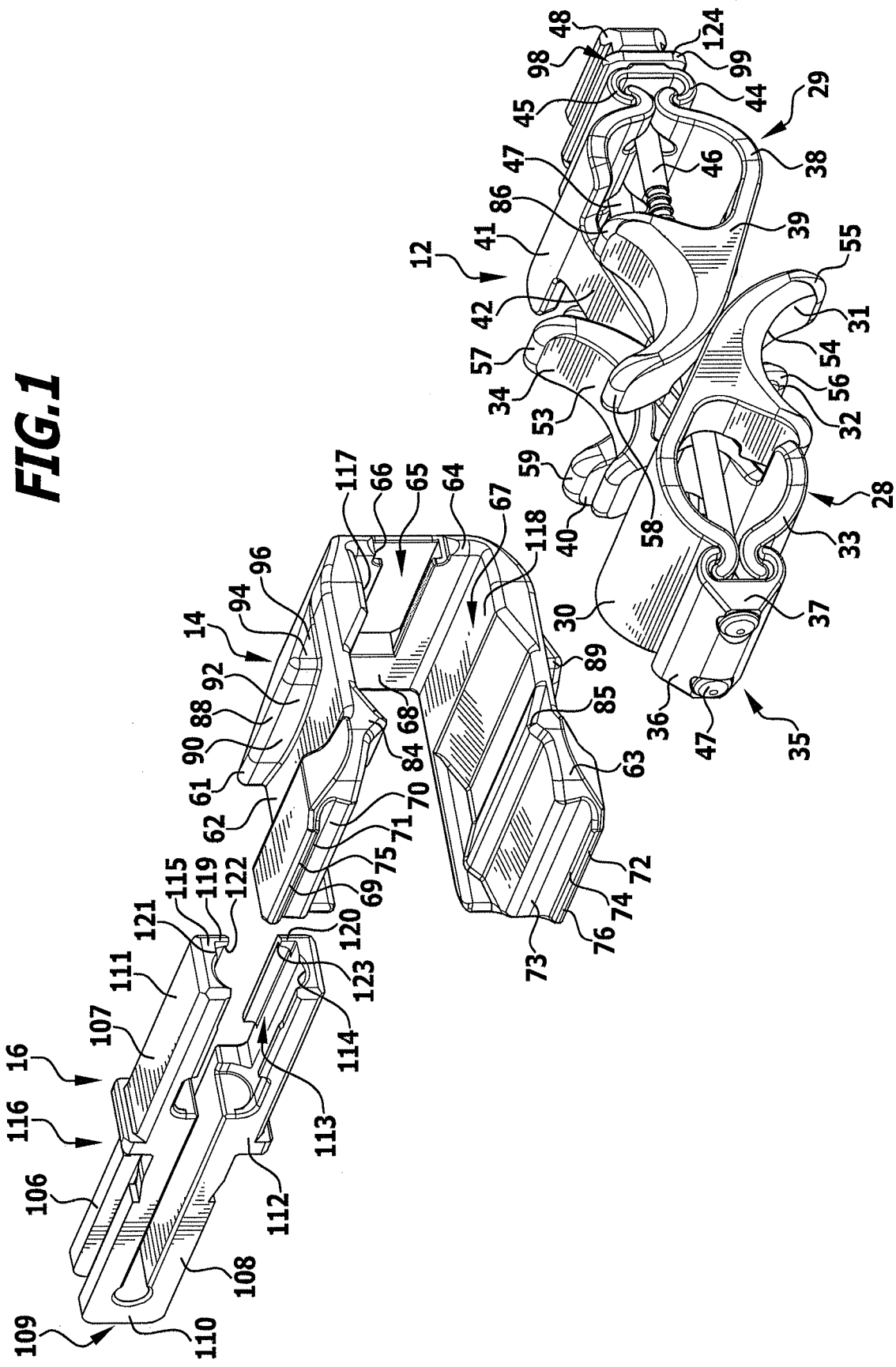

| | | | |
|---|---|---|---|
| 7,048,736 B2 | 5/2006 | Robinson | |
| 7,585,313 B2 | 9/2009 | Kwak et al. | |
| 7,585,316 B2 | 9/2009 | Trieu | |
| 7,588,592 B2 | 9/2009 | Winslow | |
| 7,727,233 B2 | 6/2010 | Blackwell | |
| 7,811,307 B2 | 10/2010 | Deneuvillers | |
| 8,012,207 B2 | 9/2011 | Kim | |
| 8,128,659 B2 | 3/2012 | Ginsberg | |
| 8,262,697 B2 | 9/2012 | Kirschman | |
| 8,313,512 B2 * | 11/2012 | Kwak et al. | 606/249 |
| 8,361,116 B2 * | 1/2013 | Edmond | 606/249 |
| 2003/0040746 A1 | 2/2003 | Mitchell | |
| 2005/0033434 A1 | 2/2005 | Berry | |
| 2005/0055031 A1 | 3/2005 | Lim | |
| 2006/0122611 A1 | 6/2006 | Morales | |
| 2006/0247640 A1 | 11/2006 | Blackwell | |
| 2007/0032790 A1 | 2/2007 | Aschmann et al. | |
| 2007/0225724 A1 | 9/2007 | Edmond | |
| 2007/0270840 A1 | 11/2007 | Chin | |
| 2007/0270856 A1 | 11/2007 | Morales | |
| 2008/0027438 A1 | 1/2008 | Abdou | |
| 2008/0086212 A1 | 4/2008 | Zucherman | |
| 2008/0108990 A1 | 5/2008 | Mitchell et al. | |
| 2008/0109082 A1 | 5/2008 | Fink et al. | |
| 2008/0114367 A1 | 5/2008 | Meyer | |
| 2008/0183211 A1 | 7/2008 | Lamborne | |
| 2008/0183218 A1 | 7/2008 | Mueller | |
| 2008/0228225 A1 | 9/2008 | Trautwein | |
| 2008/0249569 A1 | 10/2008 | Waugh | |
| 2008/0281359 A1 | 11/2008 | Abdou | |
| 2008/0281360 A1 | 11/2008 | Vittur | |
| 2008/0300601 A1 | 12/2008 | Fabian et al. | |
| 2008/0306488 A1 | 12/2008 | Altarac et al. | |
| 2009/0018658 A1 | 1/2009 | Garcia | |
| 2009/0138055 A1 | 5/2009 | Altarac et al. | |
| 2009/0149886 A1 | 6/2009 | Zentes et al. | |
| 2009/0292316 A1 * | 11/2009 | Hess | 606/249 |
| 2009/0326581 A1 * | 12/2009 | Galley et al. | 606/249 |
| 2010/0004688 A1 * | 1/2010 | Maas et al. | 606/248 |
| 2010/0131009 A1 * | 5/2010 | Roebling et al. | 606/249 |
| 2010/0198245 A1 | 8/2010 | Haas et al. | |
| 2011/0009904 A1 * | 1/2011 | Froehlich et al. | 606/249 |
| 2011/0160772 A1 | 6/2011 | Arcenio | |
| 2011/0160773 A1 * | 6/2011 | Aschmann et al. | 606/249 |
| 2012/0089184 A1 | 4/2012 | Yeh | |
| 2012/0150228 A1 | 6/2012 | Zappacosta | |
| 2012/0215261 A1 | 8/2012 | Massoudi | |
| 2012/0277796 A1 * | 11/2012 | Gabelberger et al. | 606/249 |
| 2012/0290008 A1 | 11/2012 | Kirschman | |
| 2013/0066374 A1 * | 3/2013 | Galley et al. | 606/249 |
| 2013/0184753 A1 | 7/2013 | Keiper | |

FOREIGN PATENT DOCUMENTS

| | | |
|---|---|---|
| DE | 10326690 A1 | 1/2005 |
| DE | 69828711 T2 | 1/2006 |
| DE | 10 2004 047 566 B3 | 5/2006 |
| DE | 10 2004 063 996 A1 | 8/2006 |
| DE | 20 2006018978 U1 | 3/2007 |
| DE | 10 2007 052 799 A1 | 11/2007 |
| DE | 10 2006021025 B3 | 1/2008 |
| DE | 20 2008 009 344 | 9/2008 |
| DE | 20 2008 009 344 U1 | 10/2008 |
| DE | 20 2009 001 321 | 2/2009 |
| EP | 0683653 B1 | 9/2002 |
| EP | 1297792 A1 | 4/2003 |
| EP | 2323574 B1 | 2/2012 |
| GB | 2 436 292 | 9/2007 |
| WO | WO 2006/102428 A1 | 9/2006 |
| WO | WO 2006/111174 A1 | 10/2006 |
| WO | WO 2007/070819 A2 | 6/2007 |
| WO | WO 2007/127689 A2 | 11/2007 |
| WO | WO 2009/127041 A1 | 10/2009 |
| WO | WO 2010/016949 A1 | 2/2010 |
| WO | WO 2010/019783 A2 | 2/2010 |
| WO | WO 2010/1144925 A1 | 10/2010 |
| WO | WO 2011/031924 A2 | 3/2011 |
| WO | WO 2012/035275 A1 | 3/2012 |

OTHER PUBLICATIONS

PCT International Search Report for Application No. PCT/EP2010/070361 Dated Dec. 21, 2010.
International Preliminary Report on Patentability for Application No. PCT/EP2010/070361 Dated Aug. 7, 2012.
International Search Report for Application No. PCT/EP2009/004844 dated Jan. 27, 2011.
International Search Report of International Application No. PCT/EP2009/004844. Search Completed Oct. 28, 2009 (w/English language form PCT/ISA/210 to show relevance).
Search Report from the German Patent Office for Priority Patent Application No. DE 10 2008 032 685.2; Date of the Conclusion of the Search, Jun. 8, 2009 (w/English translation of Form PCT/ISA/210).
Office Action for U.S. Appl. No. 13/558,724, dated Oct. 7, 2014.
Office Action for U.S. Appl. No. 13/891,376, dated Sep. 25, 2014.
International Search Report for PCT/EP2011/069895 mailed Feb. 15, 2012.
Office Action for U.S. Appl. No. 13/372,033, dated Nov. 8, 2011.
Office Action for U.S. Appl. No. 13/891,378, mailed May 20, 2014.
Notice of Allowance for U.S. Appl. No. 12/372,033, dated Mar. 6, 2012.
International Preliminary Report on Patentability for Application No. PCT/EP2010/070360, dated Aug. 7, 2012.

* cited by examiner

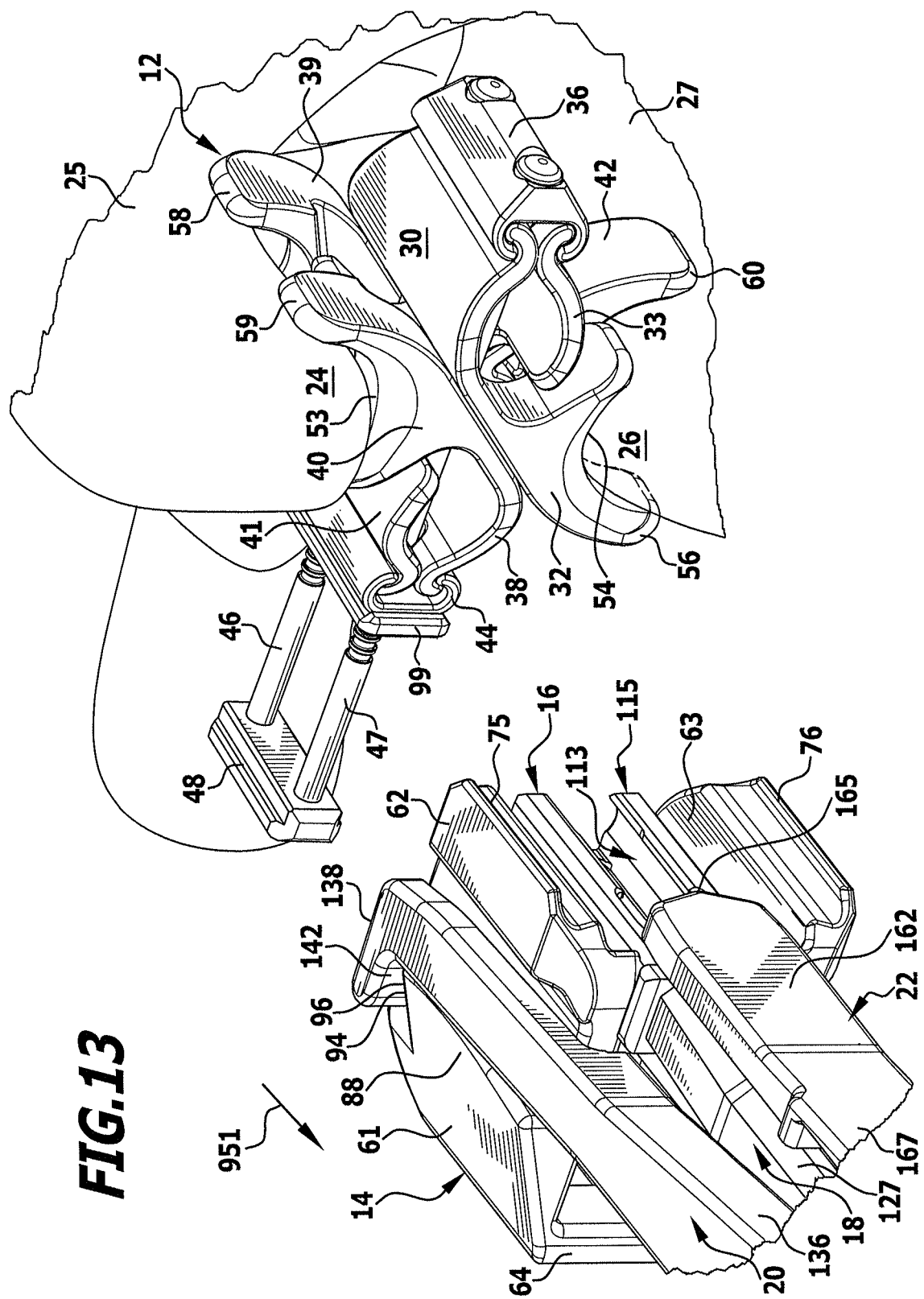

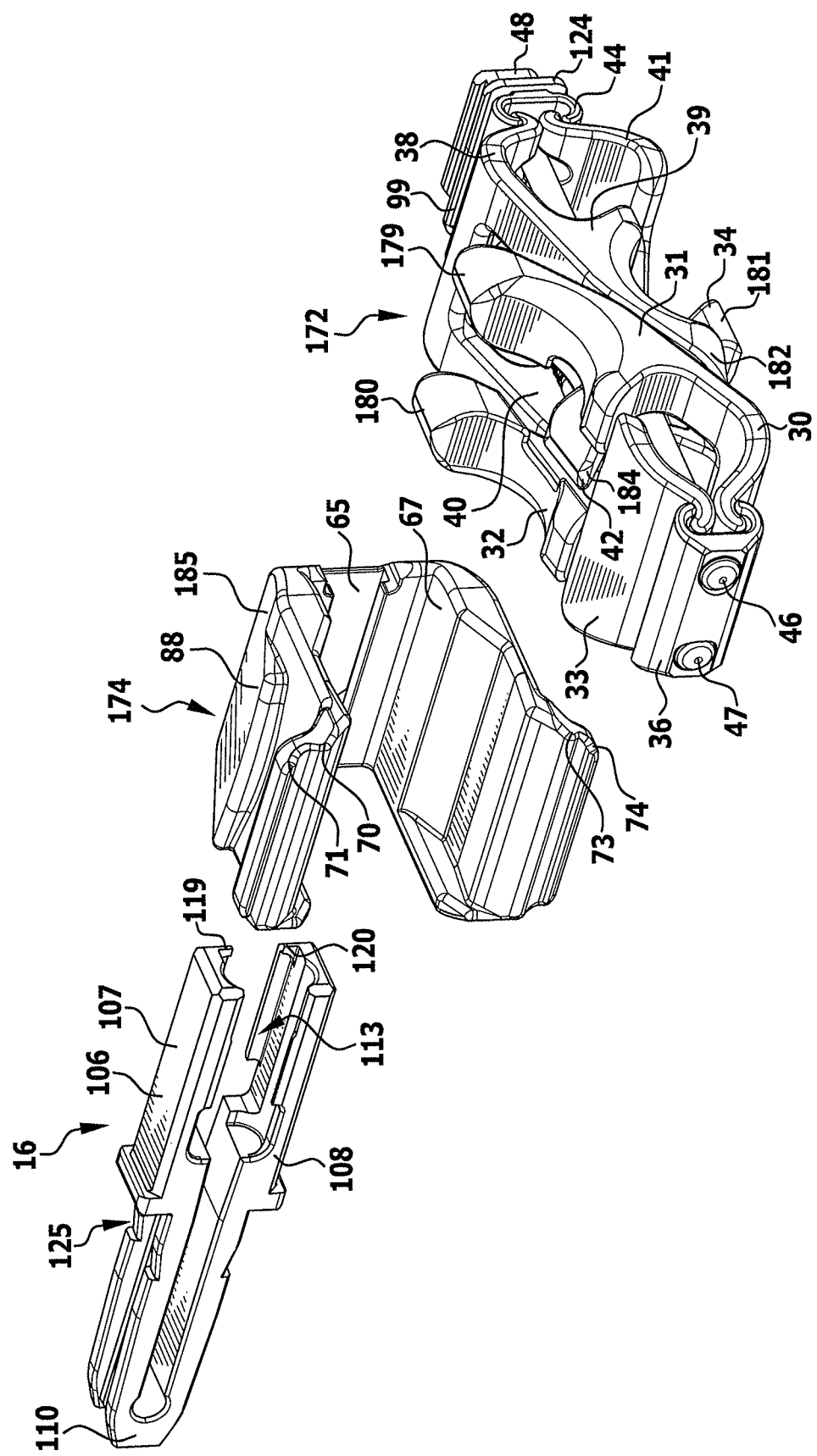

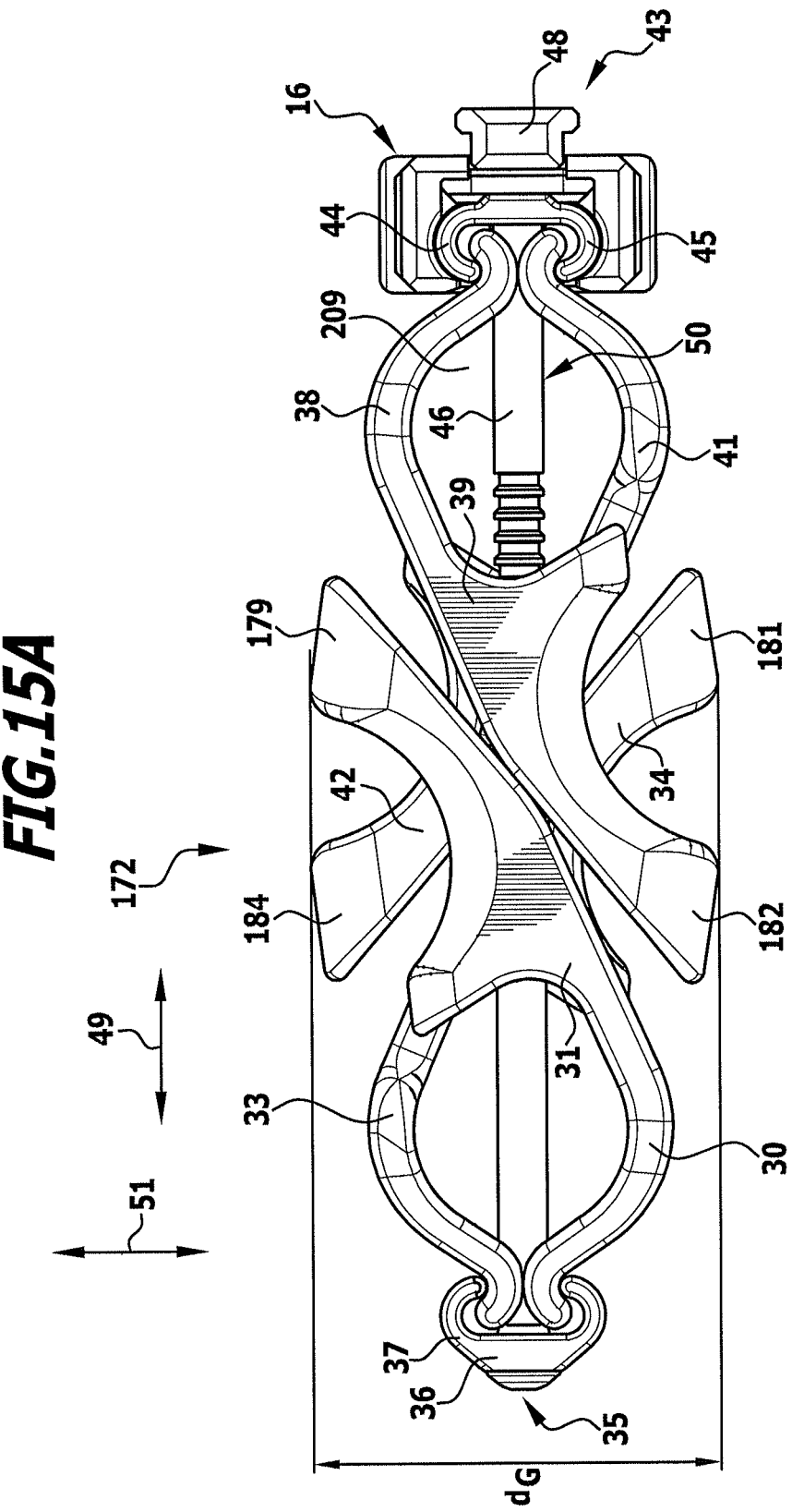

SURGICAL APPARATUS

CROSS-REFERENCE TO RELATED APPLICATIONS

This application is a continuation under 35 U.S.C. §365 of international application number PCT/EP2010/070361, filed on Dec. 21, 2010, which claims priority to German application number 10 2010 000 230.5, filed Jan. 27, 2010. The contents of both applications are incorporated by reference herein in their entirety and for all purposes.

FIELD OF THE INVENTION

The present invention relates to surgical apparatus comprising an implant for mutually supporting an upper spinous process of a first vertebral body and a lower spinous process of a second vertebral body.

Moreover, the present invention relates to surgical apparatus with a handling device for holding an implant.

BACKGROUND OF THE INVENTION

An implant of the type mentioned hereinabove is described in DE 20 2008 009 344 U1 which is incorporated herein by reference in its entirety and for all purposes. In a basic position, it can be introduced into the body through a unilateral point of entry from an introduction-side and be positioned in the inter-vertebral space between the spinous processes. By transferring the implant from the basic position into a spread position, the mutual spacing of the supporting surfaces increases so that the spinous processes resting on supporting surfaces can be pushed apart to a greater or lesser extent that are used for stabilizing neighbouring vertebral bodies relative to each other. For the lateral stabilization of the upper and the lower vertebral body, the implant comprises at least one upper supporting element as well as a lower supporting element, which can each support spinous processes on the introduction-side i.e. from the side from which the implant is introduced into the body. The supporting elements are likewise spread relative to each other when transferring the implant from the basic position into the spread position whereby, outgoing from the inter-vertebral space, they respectively approach the spinous processes. In corresponding manner, the implant may comprise at least one upper supporting element as well as at least one lower supporting element which can laterally support the upper and the lower spinous process on the body side i.e. from the side of the spinous processes remote from the introduction-side.

An object underlying the present invention is to further develop a surgical apparatus in such a way as to improve the handling thereof.

SUMMARY OF THE INVENTION

In one aspect of the invention, a surgical apparatus comprises an implant for mutually supporting an upper spinous process of a first vertebral body by means of an upper supporting surface and a lower spinous process of a second vertebral body by means of a lower supporting surface. The implant comprises a first implant component and a second implant component which is configured such as to be movable relative thereto along a clamping direction in order to transfer the implant out of a basic position in a spreading direction that is oriented transversely relative to the clamping direction into a spread position in which the upper supporting surface and the lower supporting surface are at a greater spacing from each other than in the basic position. The implant comprises at least one introduction-side upper supporting element and at least one introduction-side lower supporting element that are used for laterally supporting the upper spinous process and the lower spinous process on the introduction-side, respectively, in the spread position of the implant. The surgical apparatus comprises a fixing device for the implant that is used for spreading the at least one introduction-side upper supporting element and the at least one introduction-side lower supporting element relative to each other along the spreading direction. By means of said fixing device the implant is movable from the basic position into an introduction position in which the at least one introduction-side upper supporting element and the at least one introduction-side lower supporting element are at a greater spacing relative to each other than in the basic position. From the introduction position the implant is transferable into the spread position by moving the second implant component relative to the first implant component along the clamping direction.

In another aspect of the present invention a surgical apparatus comprises a handling device for holding an implant, in particular an implant of the type mentioned above.

BRIEF DESCRIPTION OF THE DRAWING FIGURES

Figure 2A:
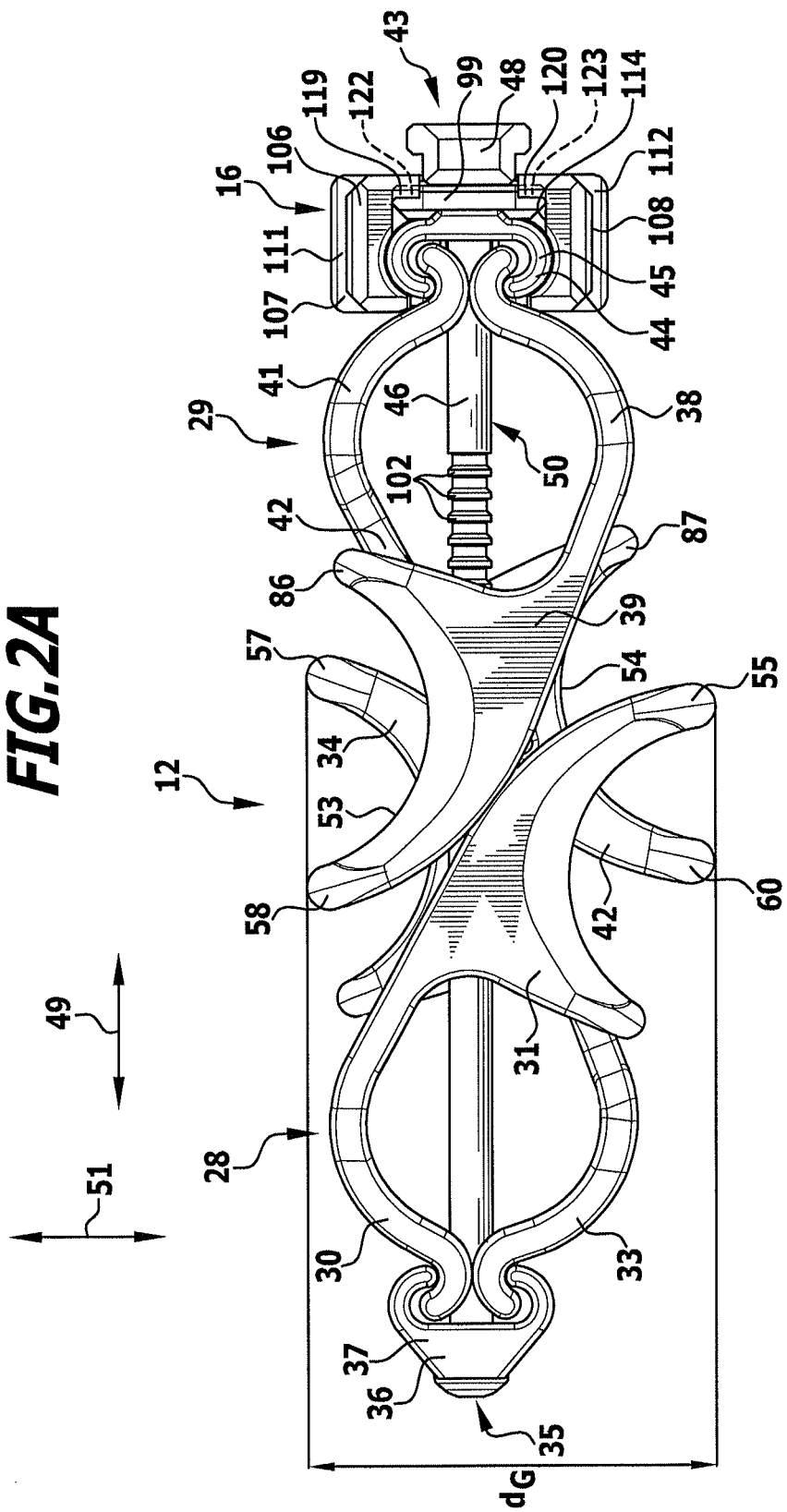
Figure 2B:
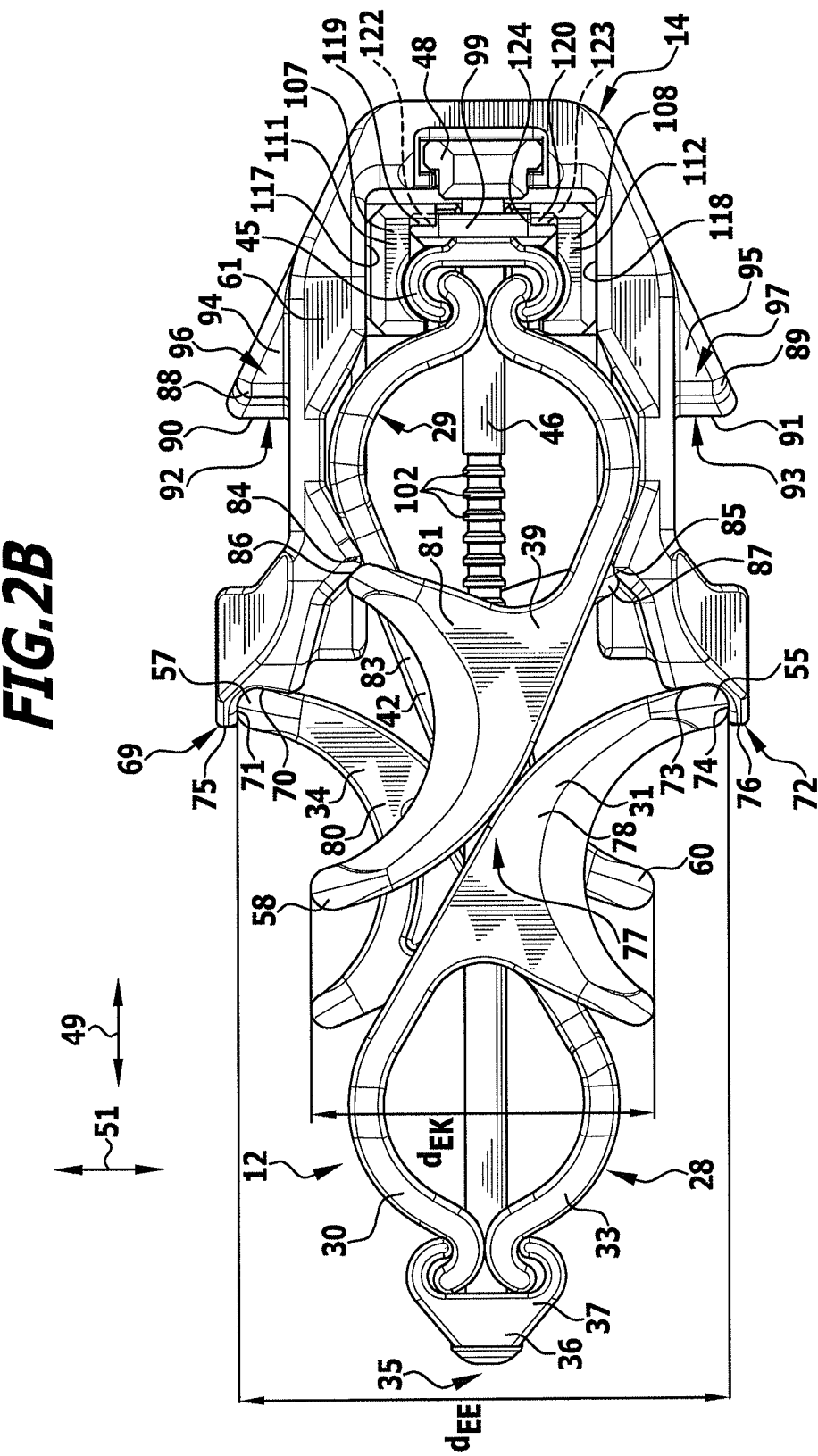
Figure 3:
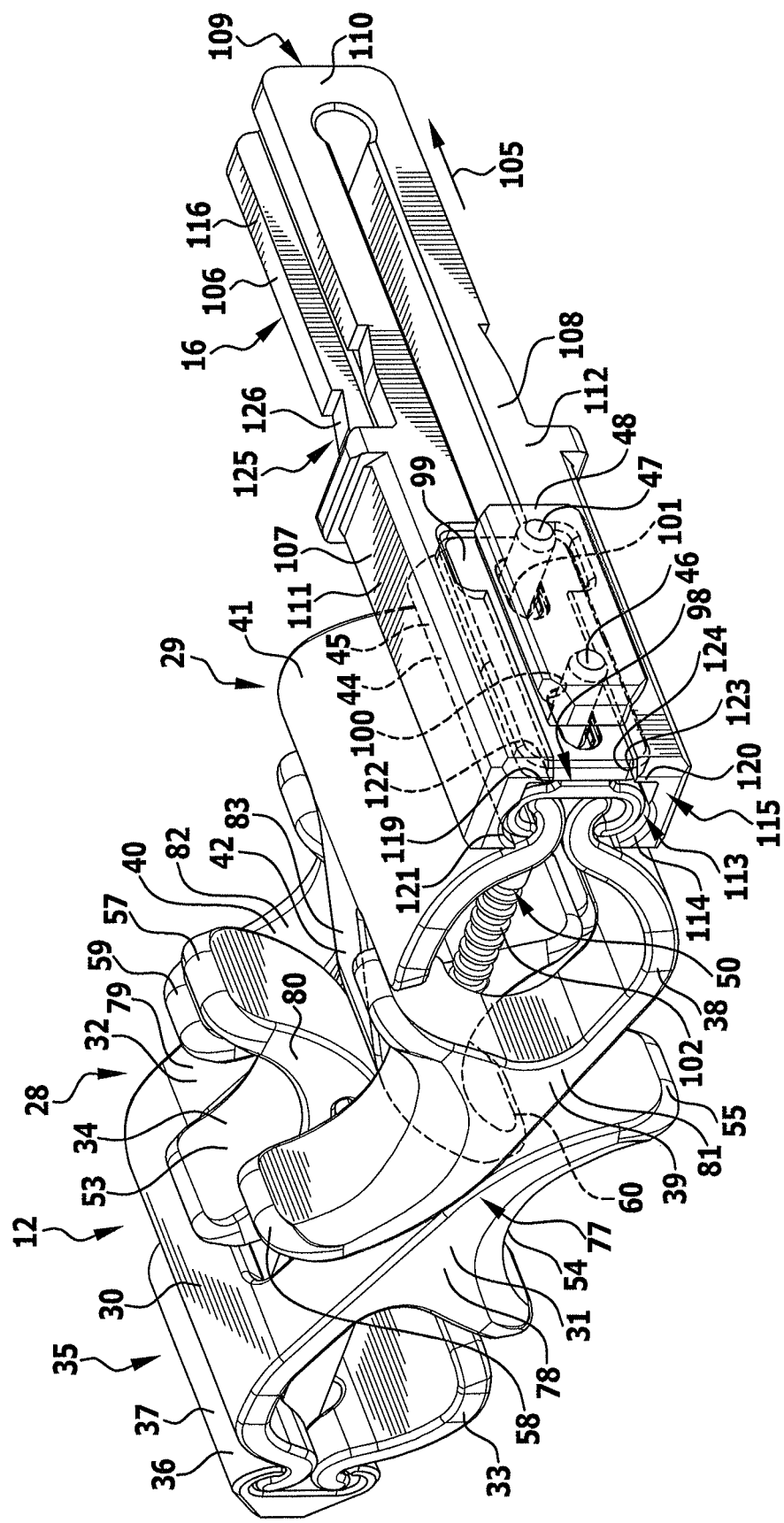
Figure 4:
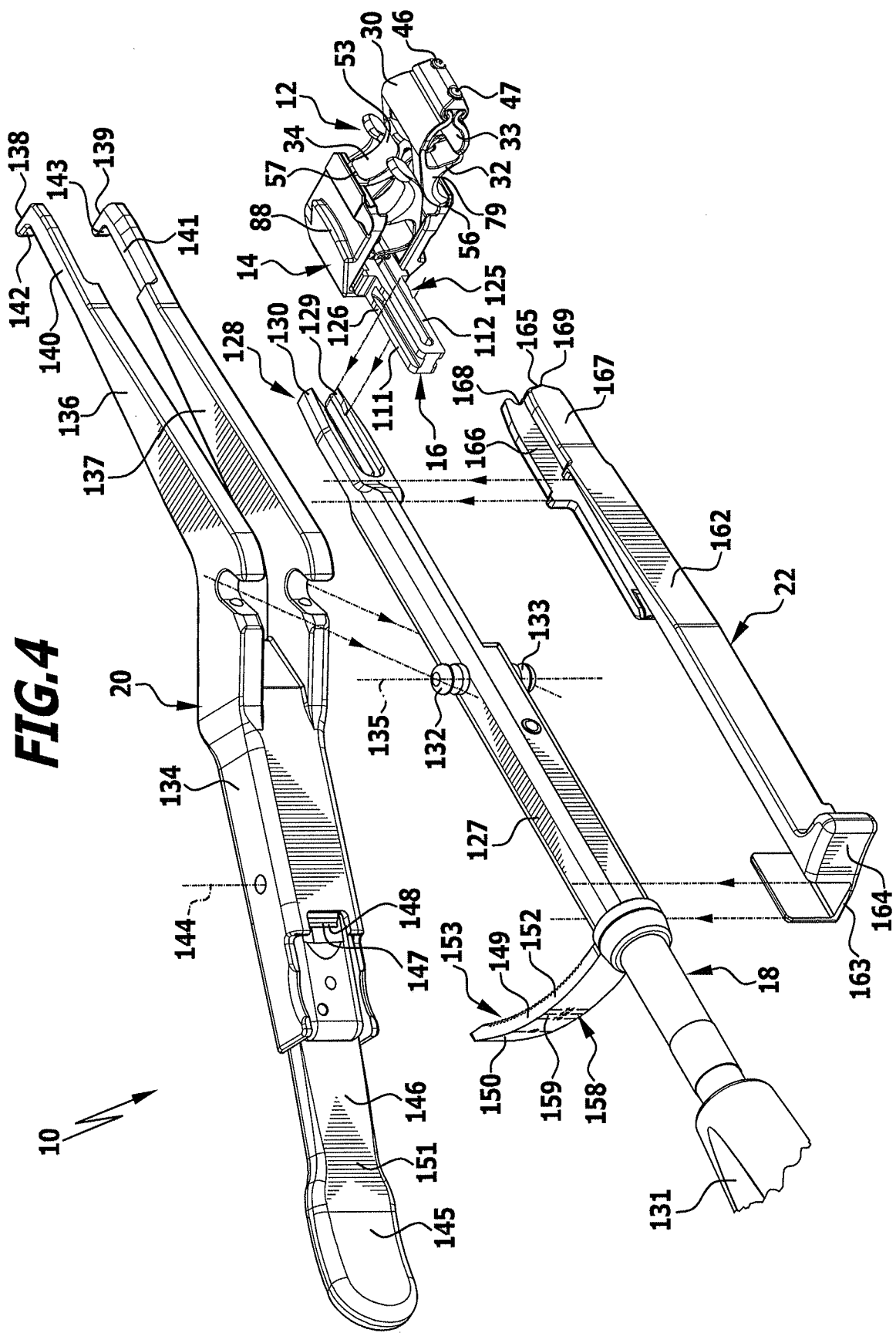
Figure 5:
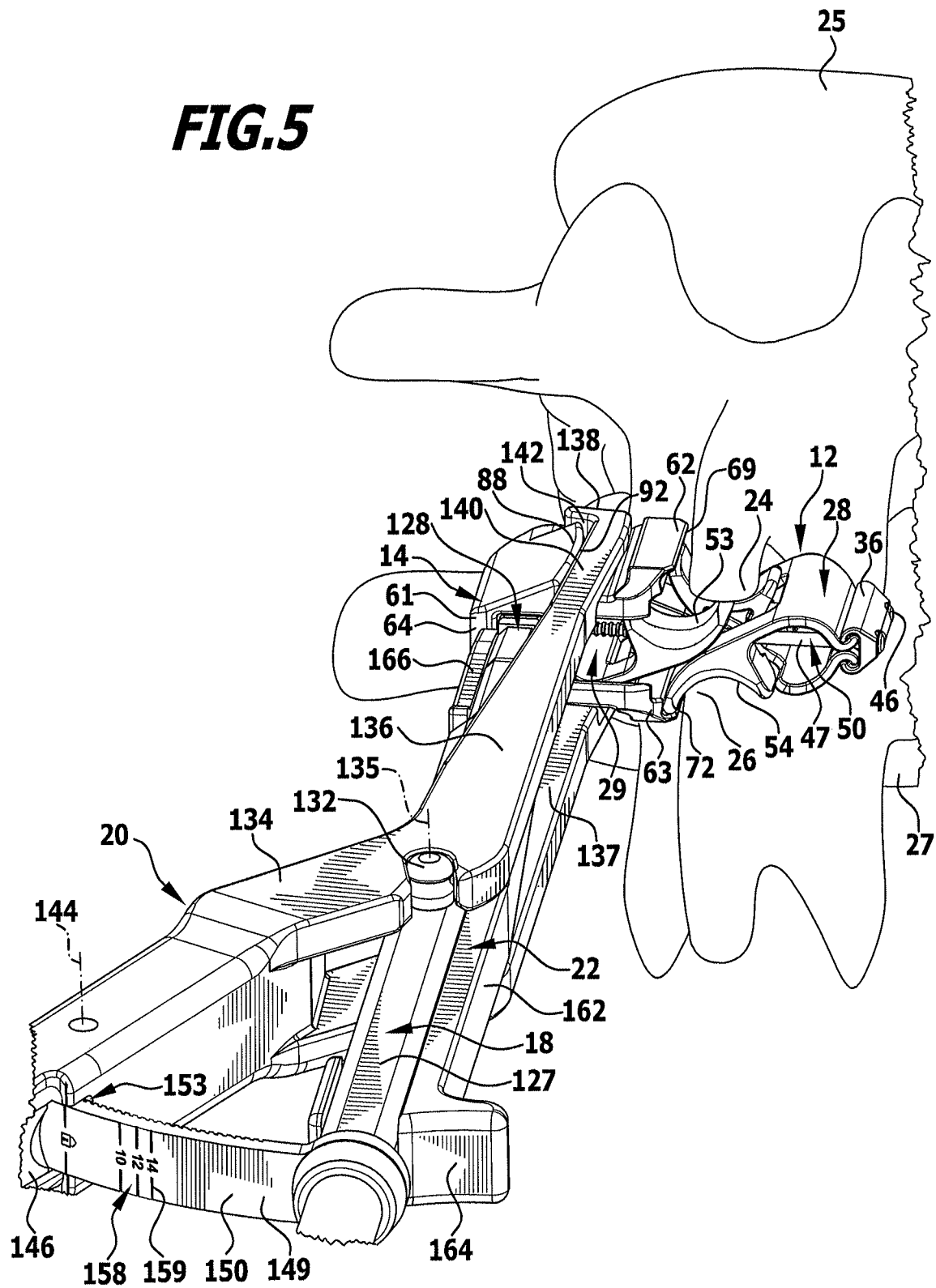
Figure 6:
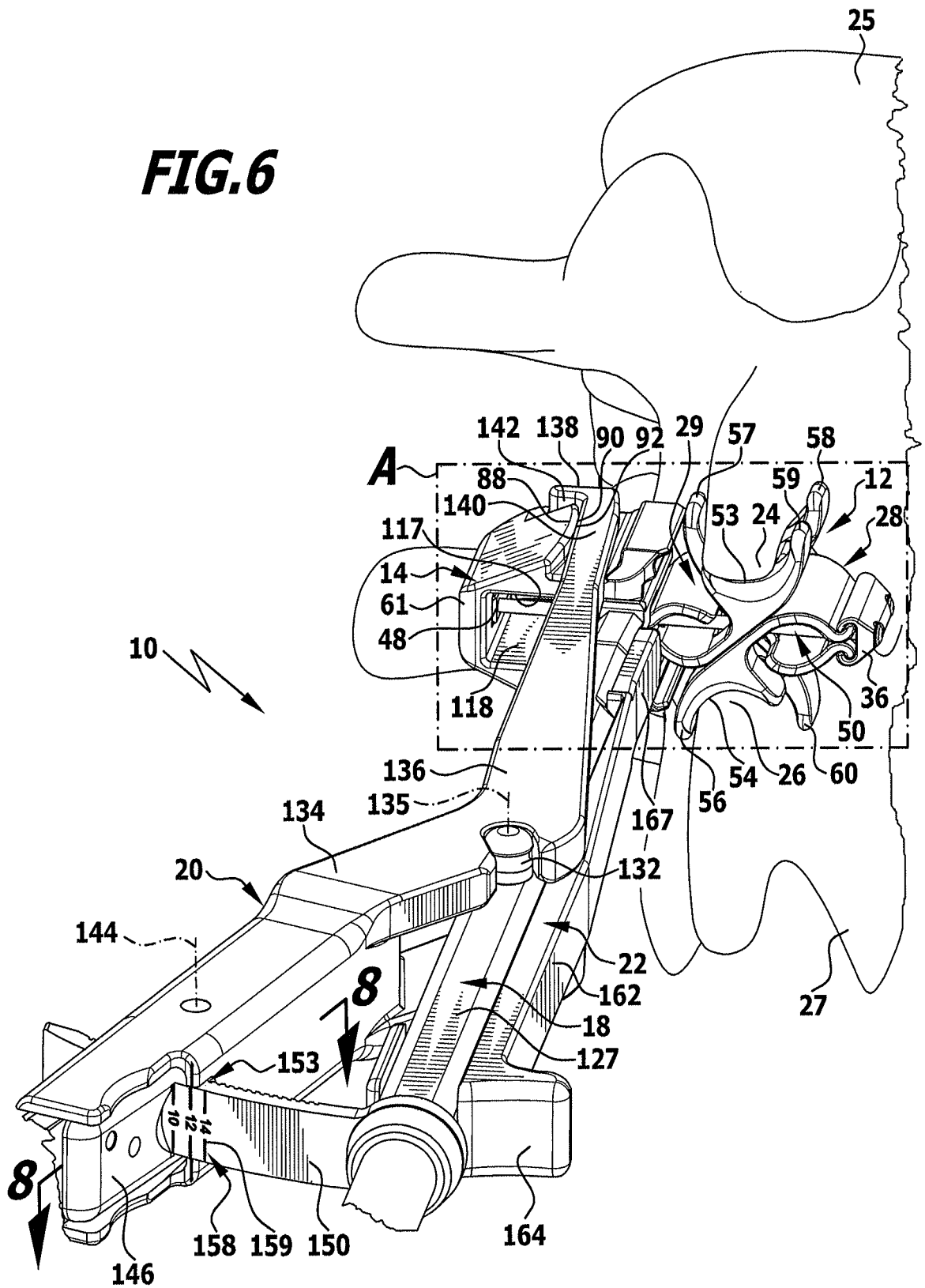
Figure 7:
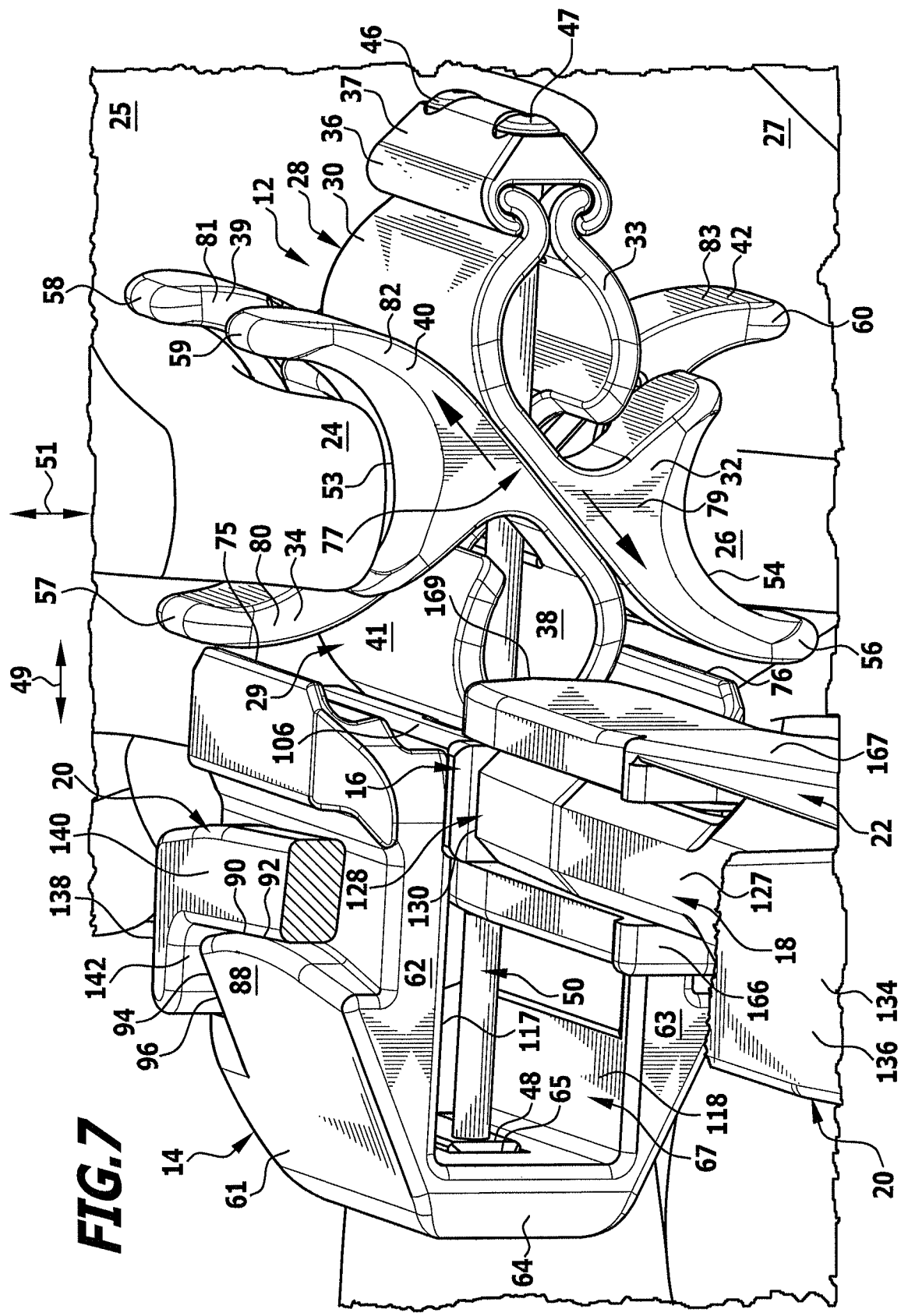
Figure 8A:
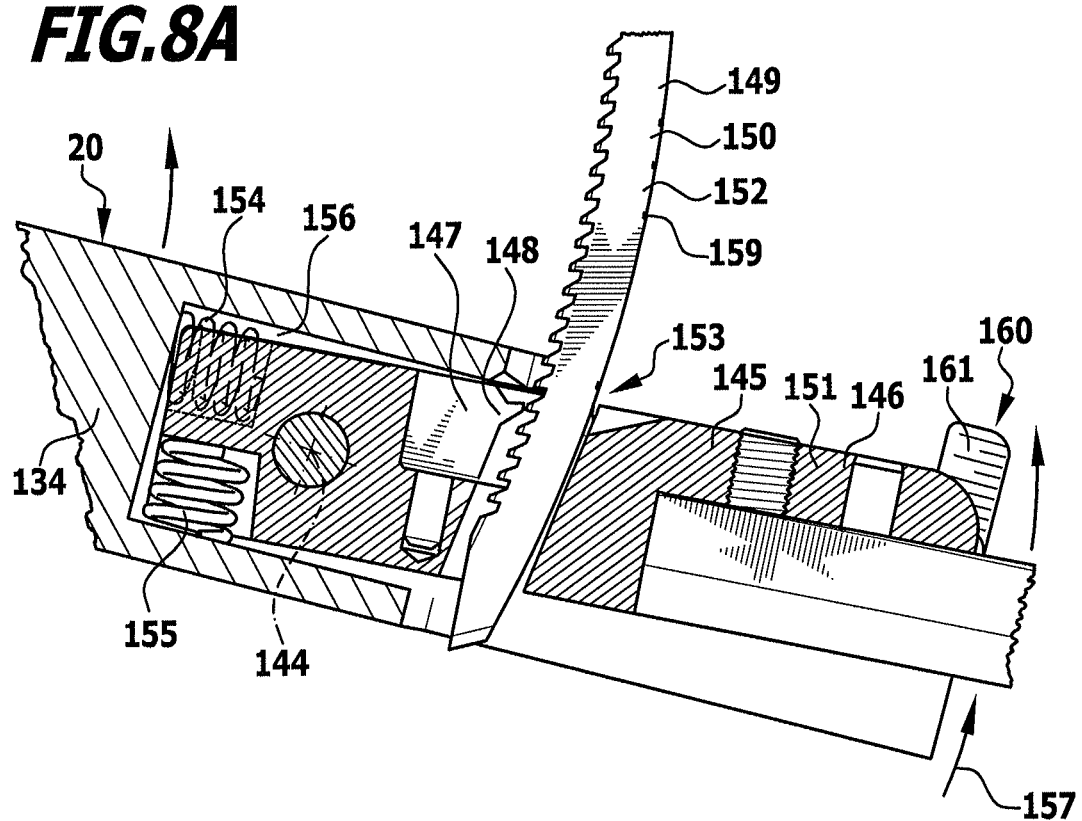
Figure 8B:
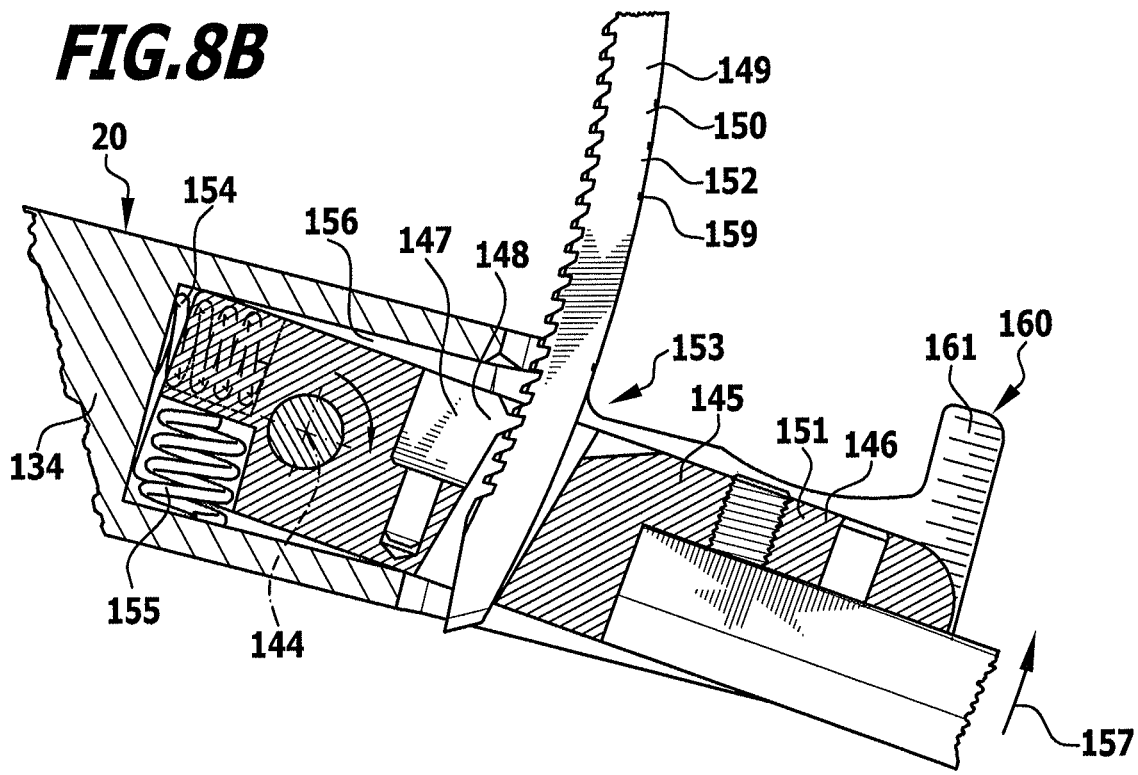
Figure 9:
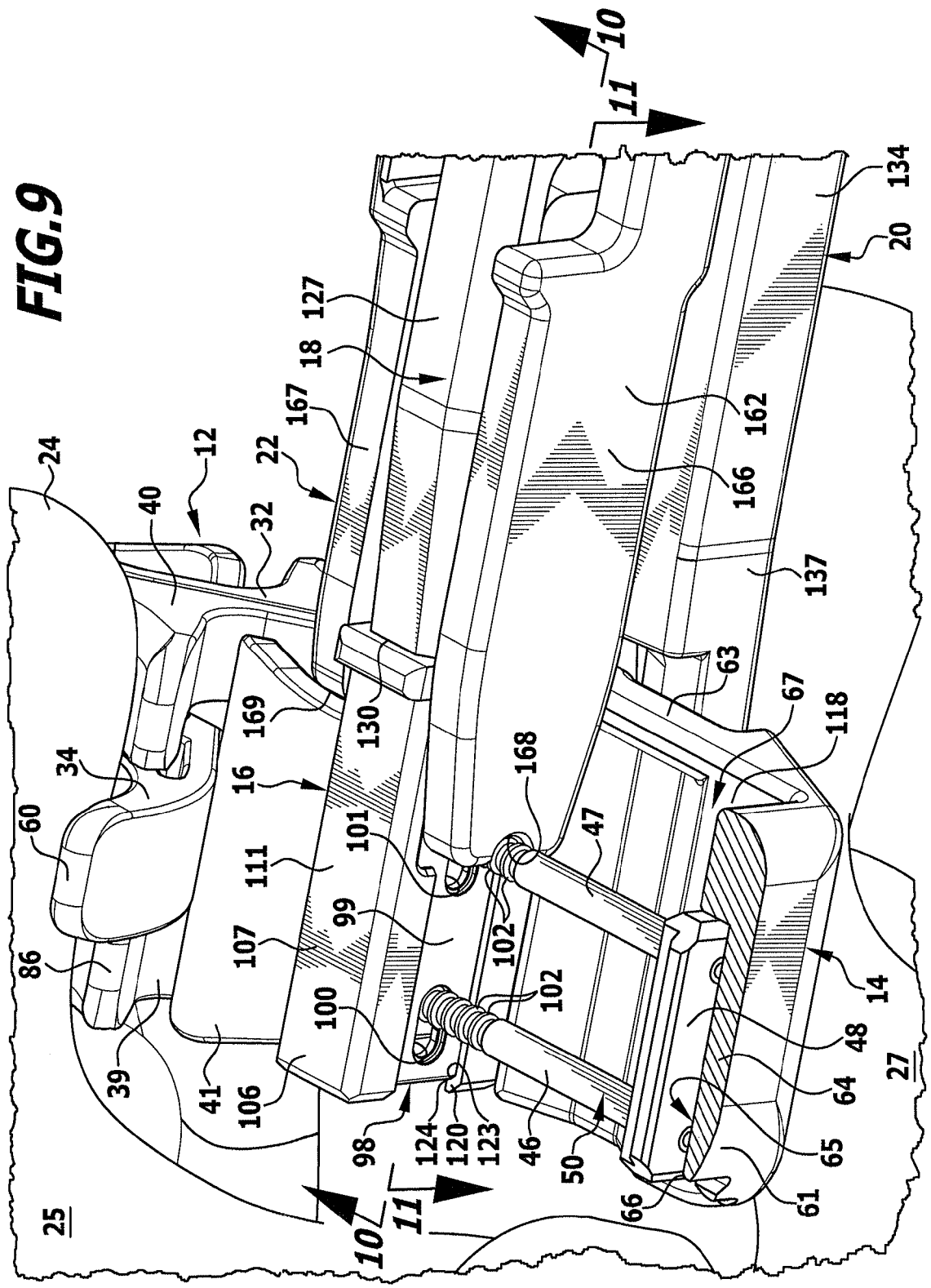
Figure 10:
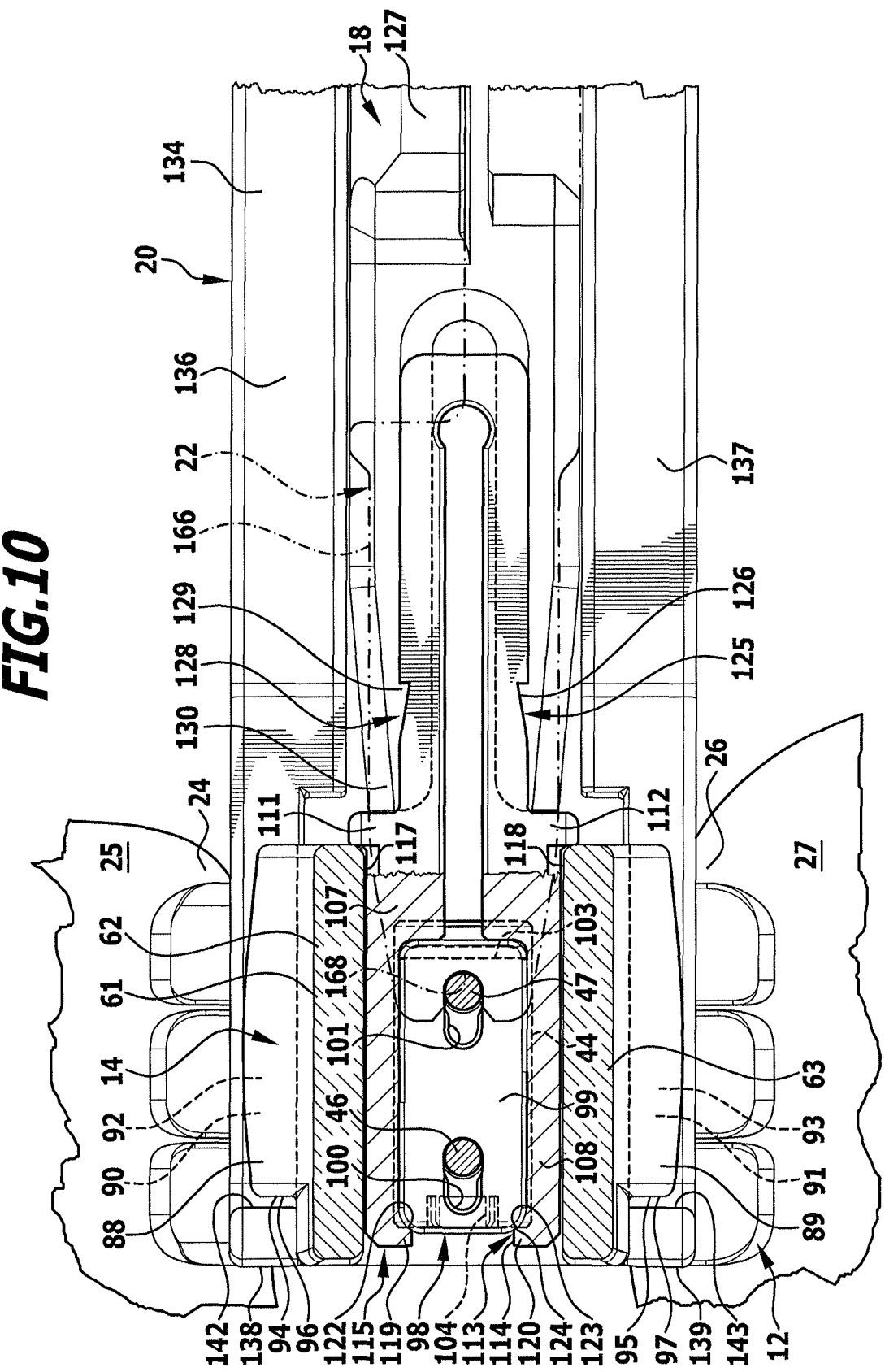
Figure 11:
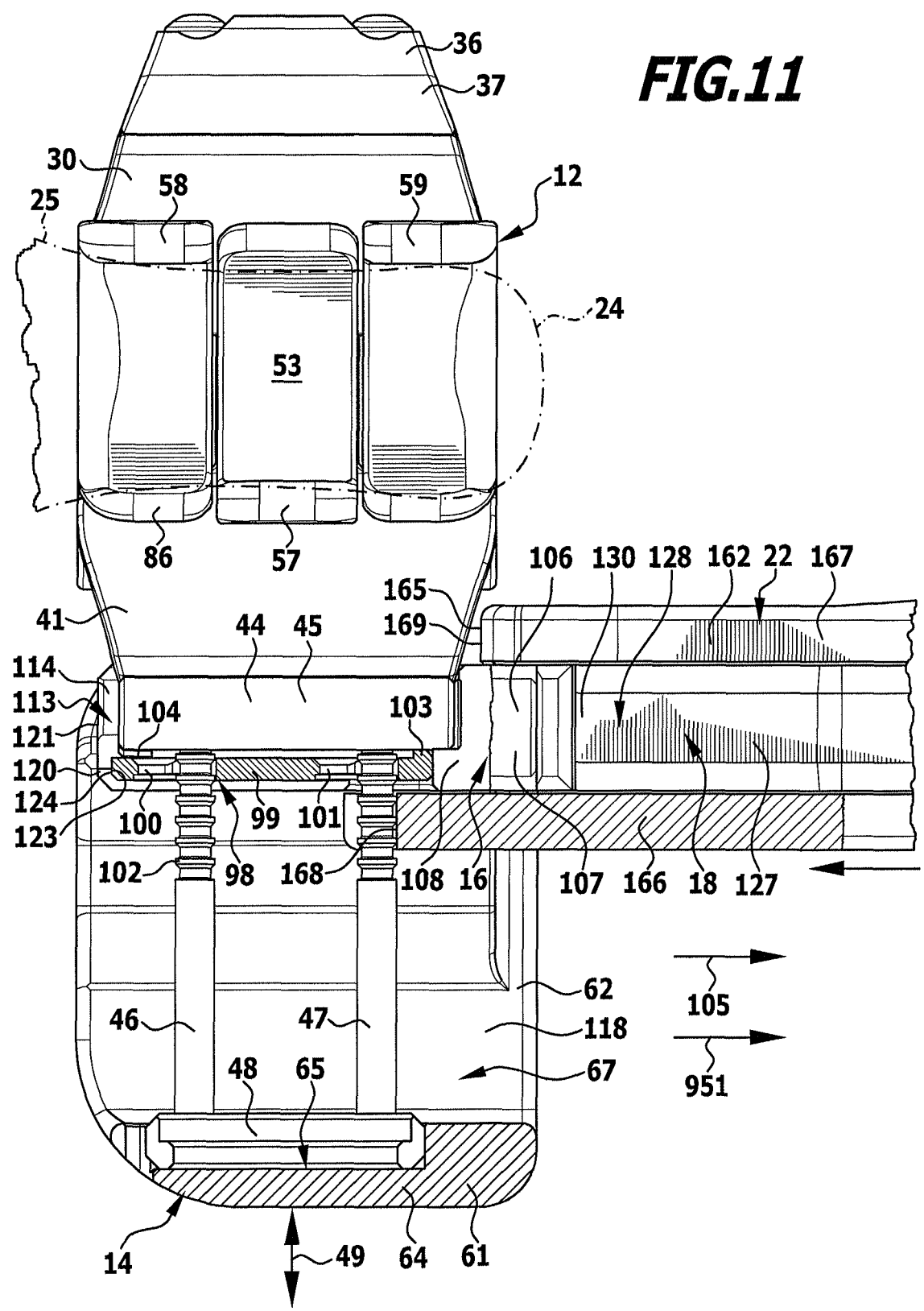
Figure 12:
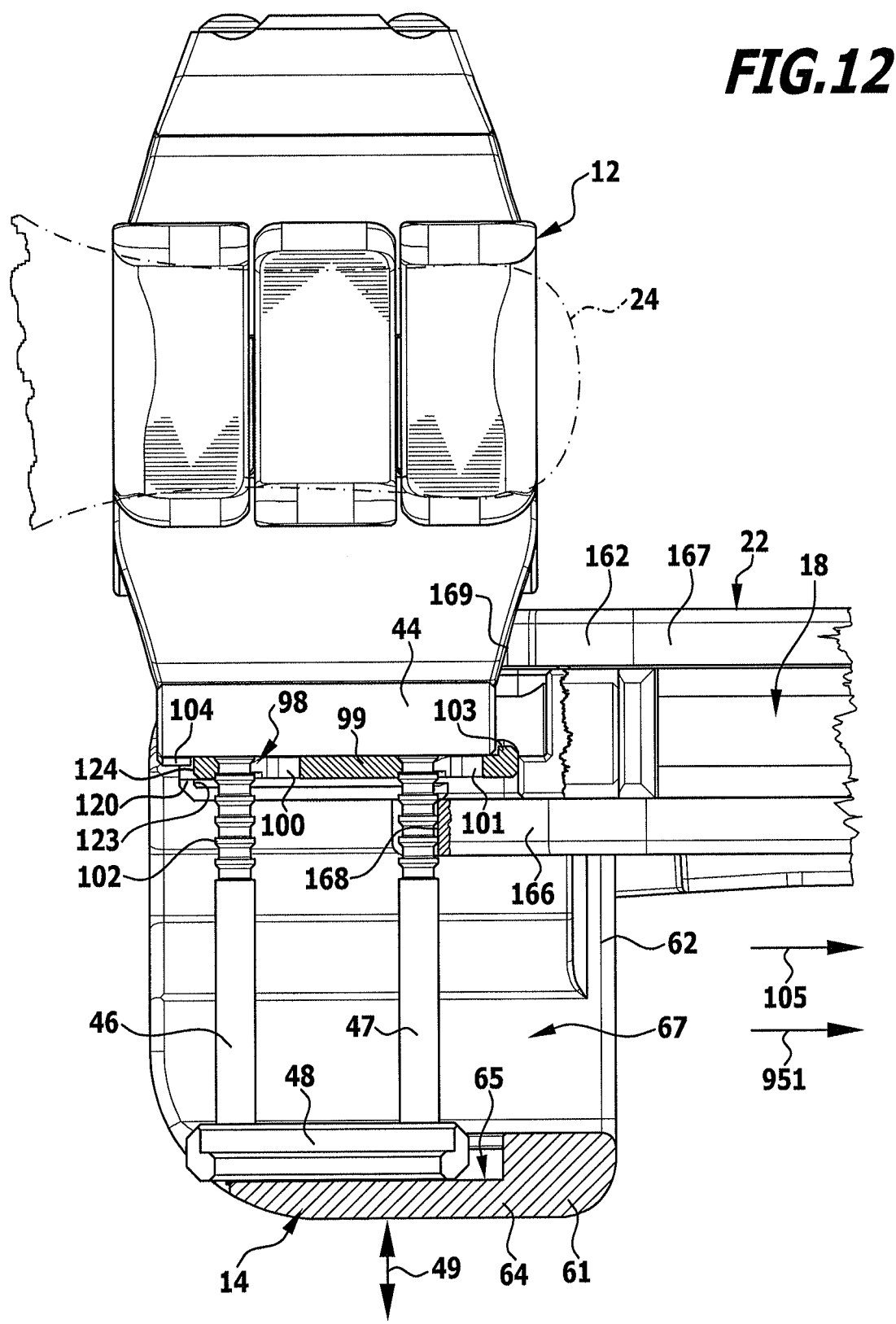
Figure 15B:
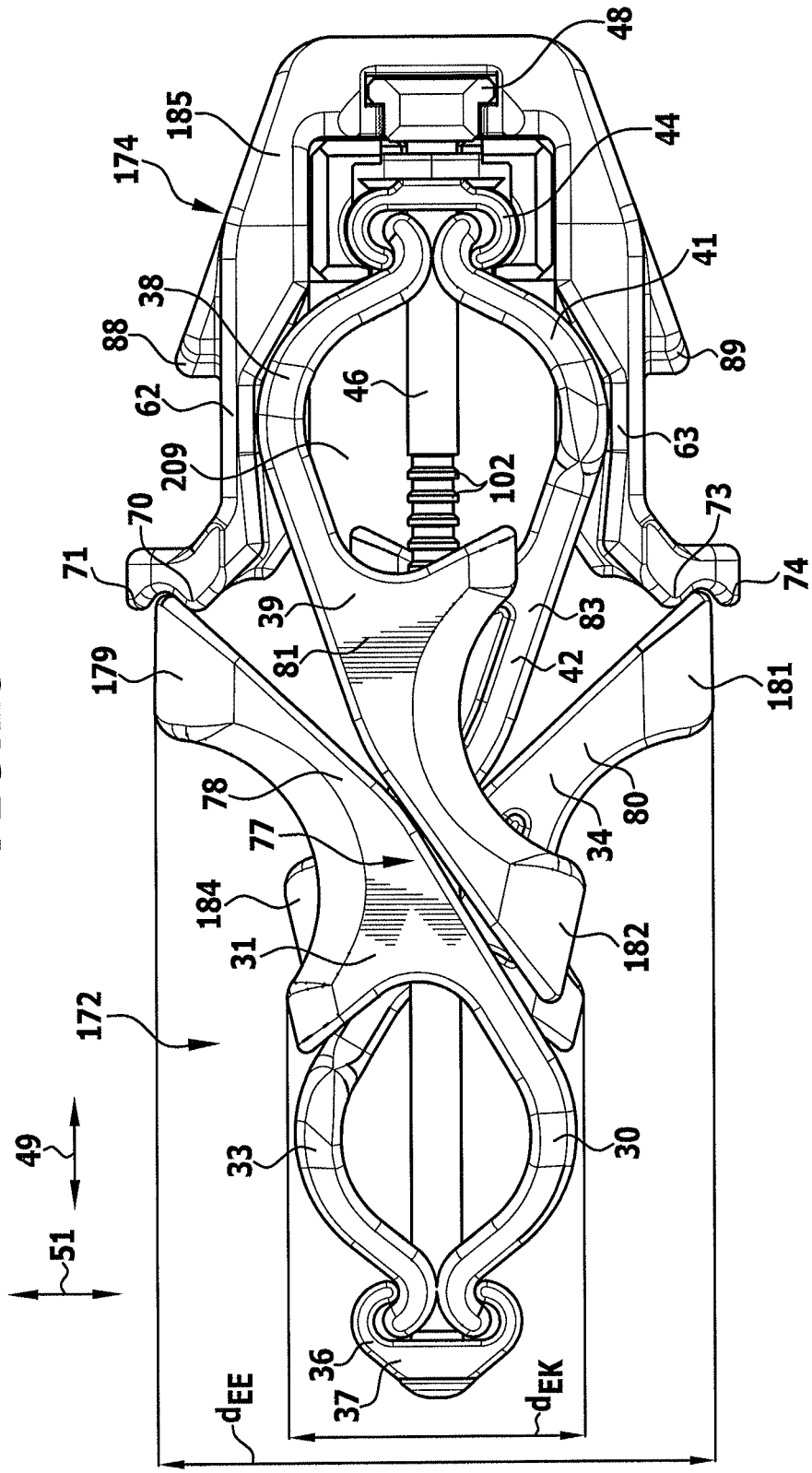
Figure 16:
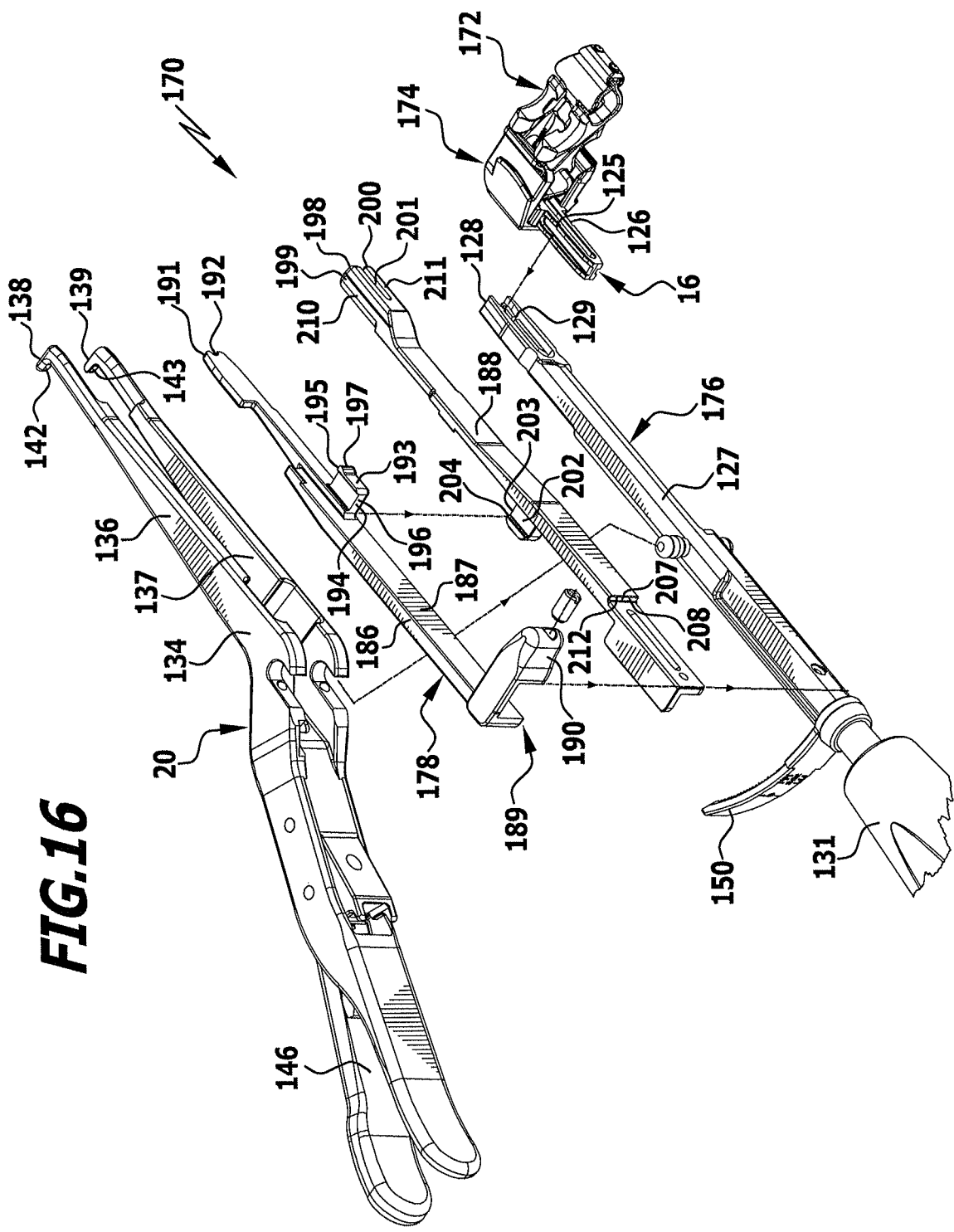
Figure 17:
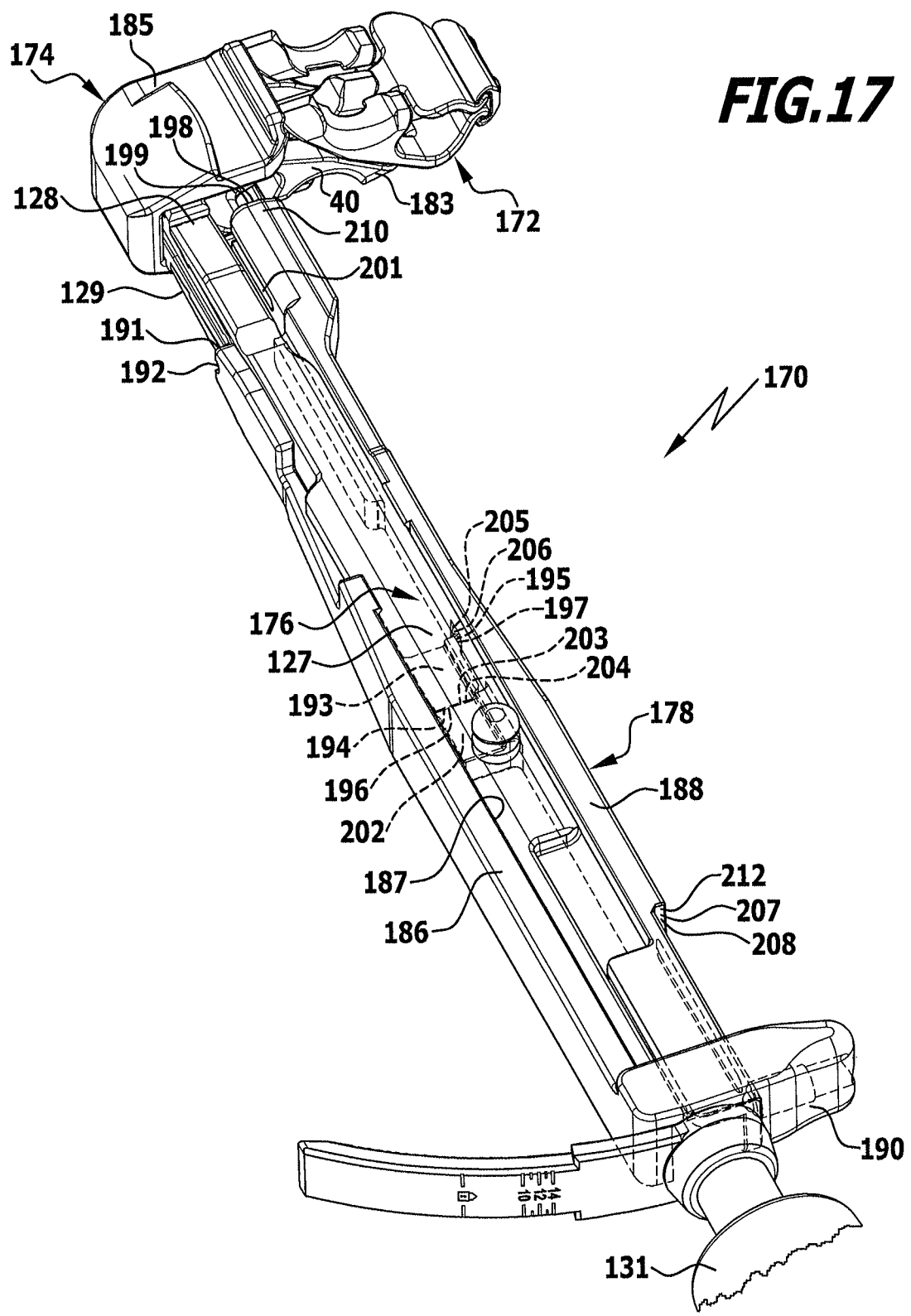
Figure 18:
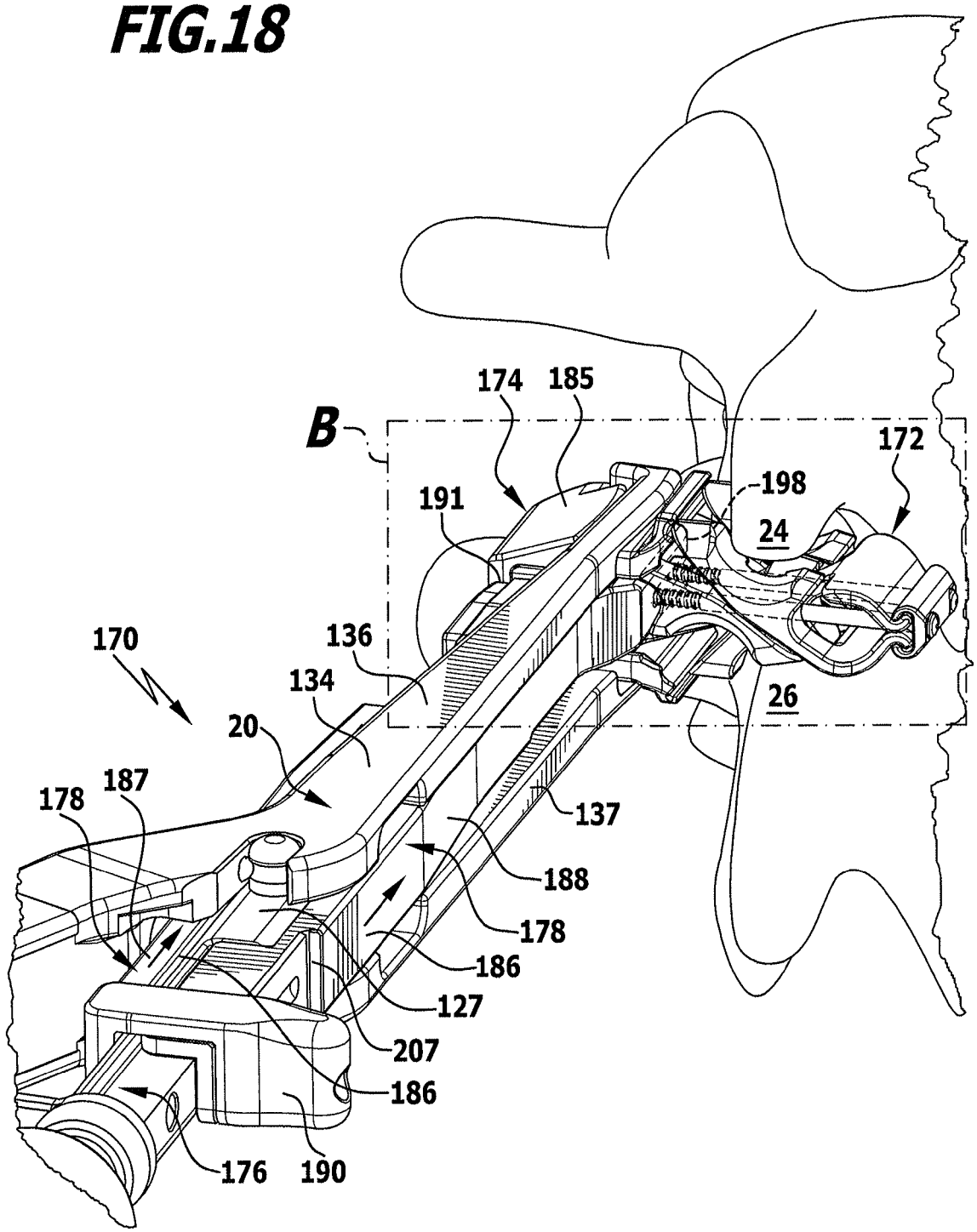
Figure 19:
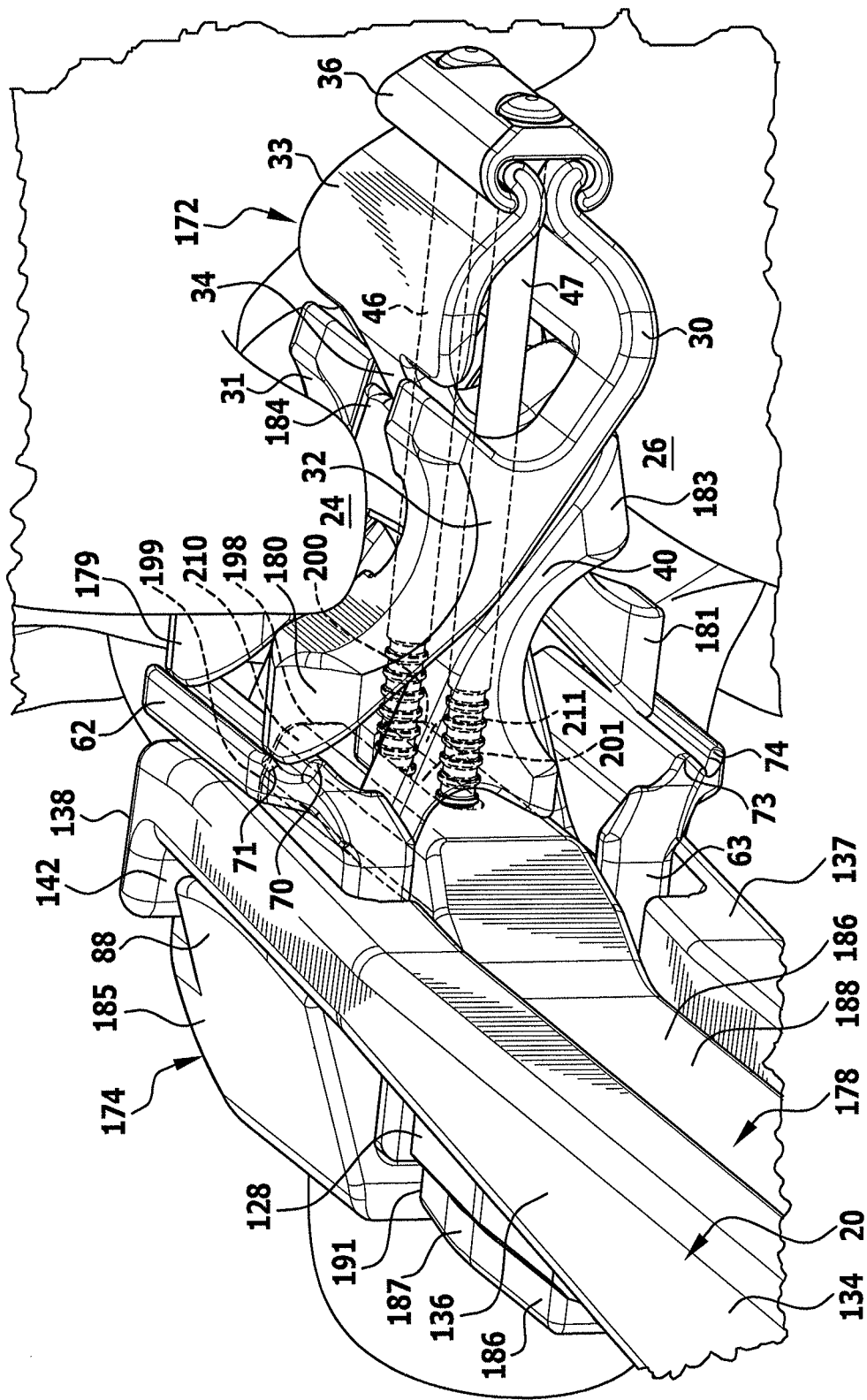
Figure 20:
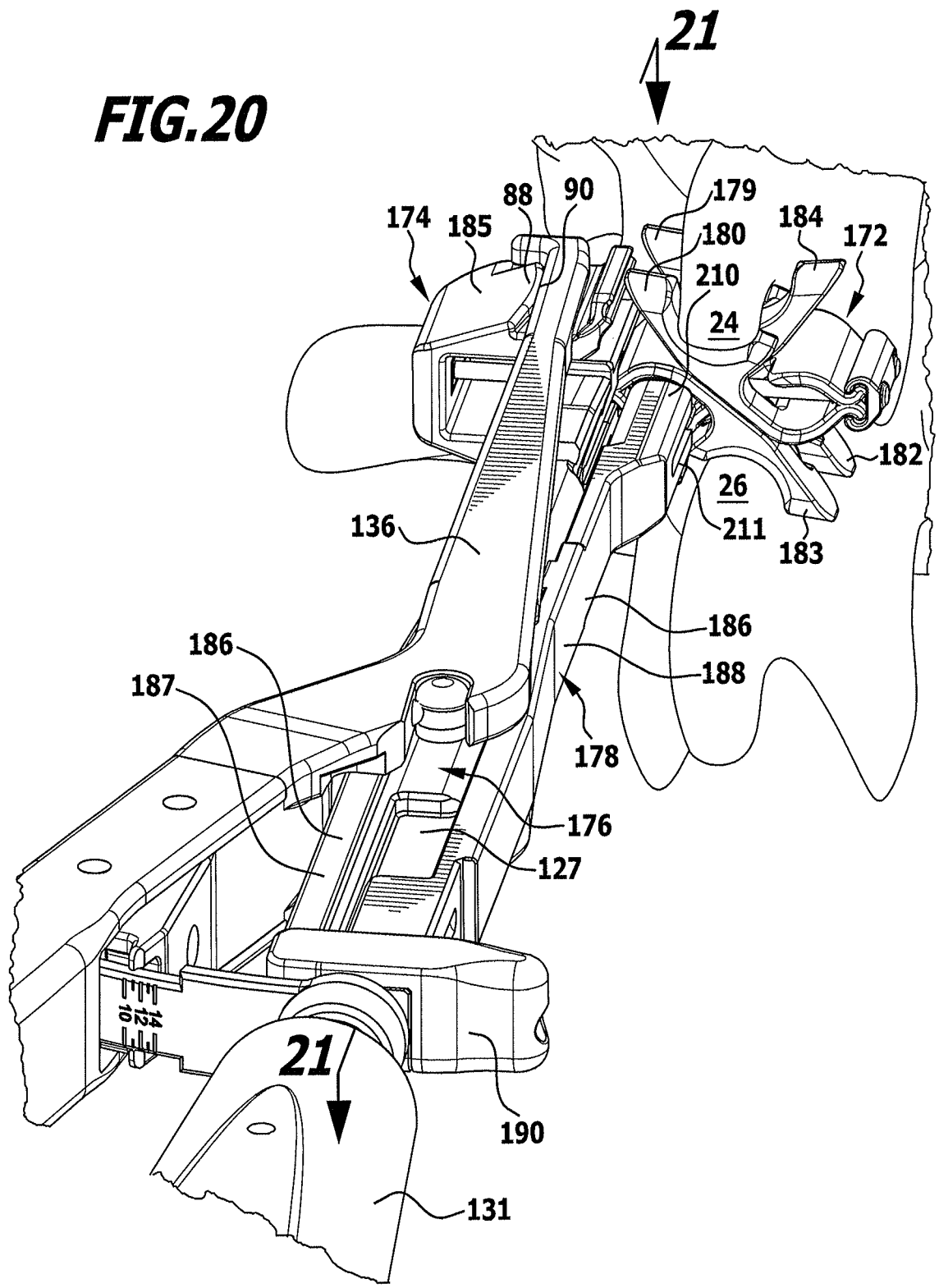
Figure 21:
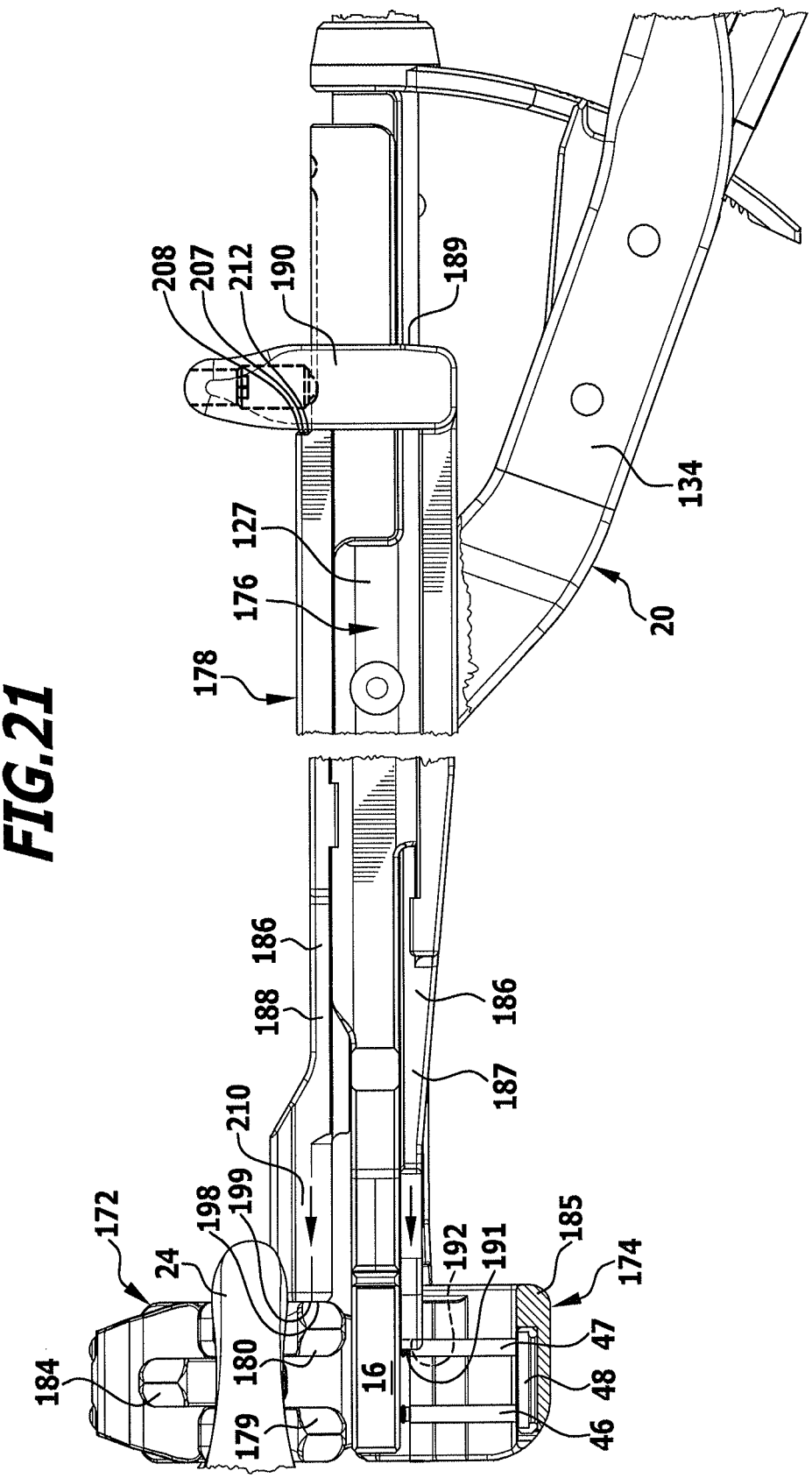

The foregoing summary and the following description may be better understood in conjunction with the drawing figures, of which:

FIG. 1: shows a perspective view of an implant, a fixing device and a holding device of surgical apparatus in a first preferred exemplary embodiment of the invention in the form of an exploded illustration;

FIG. 2A: a side view of the implant and the holding device depicted in FIG. 1 in the installed condition, wherein the implant takes a basic position;

FIG. 2B: a side view of the implant, the fixing device and the holding device depicted in FIG. 1 in the installed condition, wherein the implant takes an introduction position;

FIG. 3: a perspective illustration of the implant and the holding device depicted in FIG. 1 in the installed condition;

FIG. 4: a perspective illustration of the surgical apparatus in accordance with the first exemplary embodiment with the implant, the fixing device and the holding device depicted in FIG. 1 in the installed state and with a first, second and a third handling device in the form of an exploded illustration;

FIG. 5: the apparatus depicted in FIG. 4 when inserting the implant into a space between two spinous processes, wherein the implant adopts the introduction position;

FIG. 6: the apparatus depicted in FIG. 4 after transferring the implant from the introduction position into a spread position in which it mutually supports the spinous processes;

FIG. 7: an enlarged illustration of the detail A in FIG. 6, in a partly sectional view;

FIG. 8A: a detail view of a barring device of the apparatus along the line 8-8 in FIG. 6, wherein the barring device adopts a freeing position;

FIG. 8B: the barring device depicted in FIG. 8A in a locking position;

FIG. 9: a perspective partial view, partly sectional, of an end region of the apparatus facing the spinous processes, wherein the implant adopts the spread position in accordance with FIG. 6;

FIG. 10: a sectional view along the line 10-10 in FIG. 9;

FIG. 11: a sectional view along the line 11-11 in FIG. 9, wherein a locking element of the apparatus adopts a release position;

FIG. 12: an illustration in accordance with FIG. 11 with the locking element in the locking position and at the beginning of the detaching of the holding device and the fixing device from the implant;

FIG. 13: a perspective partial illustration of the apparatus with the implant inserted between the spinous processes, from which the fixing device and the holding device have been freed;

FIG. 14: a perspective view of an implant, a fixing device and a holding device of surgical apparatus in a second preferred exemplary embodiment of the invention in the form of an exploded illustration;

FIG. 15A: a side view of the implant and the holding device depicted in FIG. 14 in the installed state, wherein the implant adopts a basic position;

FIG. 15B: a side view of the implant, the fixing device and the holding device depicted in FIG. 14 in the installed state, wherein the implant adopts an introduction position;

FIG. 16: a perspective illustration of the surgical apparatus in accordance with the second exemplary embodiment with the implant, the fixing device and the holding device depicted in FIG. 14 in the installed state and with a first, second and a third handling device in the form of an exploded illustration;

FIG. 17: the apparatus depicted in FIG. 16 in a perspective partial illustration, without the second handling device;

FIG. 18: the apparatus depicted in FIG. 16 when inserting the implant into a space between two spinous processes, wherein the implant adopts the introduction position;

FIG. 19: an enlarged illustration of detail B in FIG. 18;

FIG. 20: the apparatus depicted in FIG. 18 after transferring the implant from the introduction position into the spread position and FIG. 21: a sectional view along the line 21-21 in FIG. 20.

DETAILED DESCRIPTION OF PREFERRED EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical apparatus comprising an implant for mutually supporting an upper spinous process of a first vertebral body by means of an upper supporting surface and a lower spinous process of a second vertebral body by means of a lower supporting surface. The implant comprises a first implant component and a second implant component which is configured such as to be movable relative thereto along a clamping direction in order to transfer the implant out of a basic position in a spreading direction that is oriented transversely relative to the clamping direction into a spread position in which the upper supporting surface and the lower supporting surface are at a greater spacing from each other than in the basic position. The implant comprises at least one introduction-side upper supporting element and at least one introduction-side lower supporting element that are used for laterally supporting the upper spinous process and the lower spinous process on the introduction-side, respectively, in the spread position of the implant. The surgical apparatus comprises a fixing device for the implant that is used for spreading the at least one introduction-side upper supporting element and the at least one introduction-side lower supporting element relative to each other along the spreading direction. By means of said fixing device the implant is movable from the basic position into an introduction position in which the at least one introduction-side upper supporting element and the at least one introduction-side lower supporting element are at a greater spacing relative to each other than in the basic position. From the introduction position the implant is transferable into the spread position by moving the second implant component relative to the first implant component along the clamping direction.

Commencing from a basic position, the implant can be moved into an introduction position by means of the fixing device. The at least one introduction-side upper supporting element and the at least one introduction-side lower supporting element thereby end up at a spacing relative to each other which is greater than their spacing from each other in the basic position of the implant. By suitable dimensioning of the fixing device, a spacing between an upper supporting element and a lower supporting element can be obtained which is greater than the spacing of the upper and the lower spinous process from each other. This leads to the fact that simply by moving the implant into the inter-vertebral space in the introduction position, the at least one introduction-side upper supporting element can come to abut the upper spinous process and the at least one lower supporting element introduction-side can come to abut the lower spinous process without it being necessary to transfer the implant into the spread position for this purpose. The supporting elements thus form stops for the spinous processes so that the maximum insertion depth of the implant into the inter-vertebral space is limited thereby. This facilitates the handling of the implant for an operating surgeon, and the supporting elements can come to abut the spinous processes in approximately the same place as they would adopt in the spread position of the implant. This means that the implant can be positioned relative to the spinous processes in an improved manner. Moreover, it is thereby ensured that an operating surgeon cannot insert the implant too deeply into the inter-vertebral space, one can therefore work less invasively and the danger of injury to the patient is reducible.

The fixing device preferably comprises a receptacle in which the implant is at least partly held. In addition or as an alternative thereto, the implant may comprise a receptacle in which the fixing device is at least partly held. The fixing device can be connected thereby to the implant so that it can be moved from the basic position into the introduction position.

It is expedient if the fixing device comprises or forms at least one first upper stop which acts in a direction opposed to the spreading direction for the at least one introduction-side upper supporting element or a carrier incorporating it and/or if the fixing device comprises or forms at least one first lower stop which acts in a direction opposed to the spreading direction for the at least one introduction-side lower supporting element or a carrier incorporating it. This provides a simple constructional possibility for mutually spreading the upper supporting element and the lower supporting element in order to increase their spacing from each other in the introduction position of the implant in comparison to the basic position of the implant.

It is of advantage if the at least one introduction-side upper supporting element or a carrier incorporating it abuts at least one first upper stop in the introduction position of the implant and/or if the at least one introduction-side lower supporting element or a carrier incorporating it abuts at least one first lower stop in the introduction position of the implant. Spreading of the upper supporting element and the lower supporting element relative to each other can thereby be ensured in a reliable manner. For this purpose, the first upper and/or the first lower stop each comprise a contact surface for the respective spreading element or the respective carrier.

It is expedient if the fixing device comprises or forms at least one second upper stop which acts in the spreading direction for the at least one introduction-side upper supporting element or a carrier incorporating it and/or if the fixing device comprises or forms at least one second lower stop which acts in the spreading direction for the at least one introduction-side lower supporting element or a carrier incorporating it. It can thereby be ensured in a simple constructional way that, in the introduction position, the upper and the lower supporting element will not exceed a maximum spacing along the spreading direction which is given by the spacing of the second upper stop and the second lower stop from each other. This makes it possible to prevent the implant from being damaged in the introduction position.

It is of advantage if the at least one introduction-side upper supporting element or the carrier incorporating it abuts the at least one second upper stop in the introduction position of the implant and/or if that the at least one introduction-side lower supporting element or a carrier incorporating it abuts the at least one second lower stop in the introduction position of the implant. It can thereby be ensured in a reliable manner that the upper supporting element and the lower supporting element cannot be spread apart along the spreading direction to such an extent that the implant will be damaged. For this, the second upper and/or the second lower stop each comprise a contact surface for the respective supporting element or the respective carrier.

In particular, provision may be made for the at least one introduction-side upper supporting element to be arranged in positively-locking manner between the at least one first upper stop and the at least one second upper stop in the introduction position of the implant and for the at least one introduction-side lower supporting element to be arranged in positively-locking manner between the at least one first lower stop and the at least one second lower stop in order to ensure reliable fixing of the implant.

It is expedient if the fixing device comprises or forms at least one introduction-side upper bone stop element for the upper spinous process and/or if the fixing device comprises or forms at least one introduction-side lower bone stop element for the lower spinous process. This facilitates the handling of the implant. When inserting the implant into the inter-vertebral space, the implant can abut not only the upper or the lower spinous process by means of the upper and the lower supporting element, but it can also do so by means of the fixing device. In consequence, more reliable positioning of the implant relative to the spinous processes is attainable.

Expediently, in the introduction position of the implant, the upper bone stop element and the lower bone stop element are spaced further apart relative to each other than the introduction-side upper supporting element and the introduction-side lower supporting element in order to facilitate handling of the implant in the inter-vertebral space.

Provision may be made for the first implant component to comprise the at least one introduction-side upper supporting element and the at least one introduction-side lower supporting element. In practice, this has proved to be advantageous for a simpler construction of the implant.

As an alternative or in addition thereto, provision may be made for the second implant component to comprise at least one introduction-side upper supporting element and/or at least one introduction-side lower supporting element.

Preferably, the implant comprises at least one body-side upper supporting element and at least one body-side lower supporting element for laterally supporting of the upper spinous process and/or the lower spinous process on the body-side, respectively, in the spread position of the implant. As previously mentioned, "body-side" in the present context is to be interpreted as being that lateral side of the spinous processes which is remote from the lateral side of the spinous processes towards which the implant is introduced into the body. The upper supporting element and the lower supporting element enable the upper and the lower spinous process to be provided with lateral support on the body side and thus too, more reliable support thereof relative to each other.

Provision may be made for the second implant component to comprise at least one body-side upper supporting element and at least one body-side lower supporting element. In practice, this has proved to be advantageous for a simpler constructional arrangement of the implant.

As an alternative or in addition thereto, provision may be made for the first implant component to comprise at least one body-side upper supporting element and/or at least one body-side lower supporting element.

It is preferred, that the surgical apparatus comprise a coupling device having at least one first coupling element which is coupled to an introduction-side supporting element as well as having at least one second coupling element which is coupled to a body-side supporting element and which, in the introduction position of the implant, cooperates with the at least one first coupling element for decreasing the spacing of the at least one body-side upper supporting element and the at least one body-side lower supporting element from each other relative to their spacing from each other in the basic position of the implant. In the introduction position of the implant, the at least one introduction-side upper supporting element and the at least one introduction-side lower supporting element are at a greater spacing from each other than in the basic position of the implant. This can be ensured by means of the fixing device. By means of the additional coupling device in the present exemplary embodiment furthermore, it is possible to reduce the spacing of the at least one body-side upper supporting element and the at least one body-side lower supporting element from each other in the introduction position of the implant relative to their spacing from each other in the basic position of the implant. This provides the possibility of reducing the insertion depth of the implant by means of the fixing device and the coupling device. This thereby makes it easier for the operating surgeon when inserting the implant into the inter-vertebral space. Moreover, this also reduces the danger of the operating surgeon inadvertently knocking against the spinous processes or other body structures, e.g. ligaments, tendons or muscles during the insertion of the implant. This facilitates the handling of the implant considerably. In order to couple an introduction-side supporting element to a body-side supporting element, the coupling device comprises the at least one first coupling element and the at least one second coupling element which cooperate in the introduction position of the implant.

The first and/or the second coupling element can, for example, be connected respectively to the introduction-side and the body-side supporting element, especially in one piece manner, in order to be coupled thereto.

It is expedient if the implant comprises or forms the coupling device because this then lends itself to the provision of the surgical apparatus with a simpler construction.

Provision can be made, in particular, for the first implant component to comprise the at least one first coupling element and for the at least one second implant component to comprise the at least one second coupling element.

Preferably, the coupling device comprises a first coupling element that is coupled to an introduction-side upper supporting element and a second coupling element which cooperates therewith and is coupled to a body-side lower supporting element. In the introduction position of the implant, the effect of the fixing device and the coupling device with reference to the introduction-side upper supporting element and the body-side lower supporting element run counter to one another along the spreading direction. The further the introduction-side upper supporting element is spread relative to an introduction-side lower supporting element under the effect of the fixing device, the closer the body-side lower supporting element approaches a body-side upper supporting element. In practice, it has been shown that the coupling device in this exemplary embodiment can be of simple construction and that reliable functioning of the coupling device can be ensured.

In corresponding manner, it is expedient for the achievement of the same advantage if the coupling device comprises a first coupling element which is coupled to an introduction-side lower supporting element and second coupling element which cooperates therewith and is coupled to a body-side upper supporting element.

Preferably, the at least one first coupling element and/or the at least one second coupling element form at least partly a supporting surface for a spinous process. The first and/or the second coupling element can thereby exercise an additional function. This permits the implant to be provided with a more compact form of construction.

It is expedient if the coupling device comprises a first coupling element for an introduction-side upper supporting element and a first coupling element for an introduction-side lower supporting element which, in the introduction position of the implant, are spread further relative to each other along the spreading direction by means of the fixing device than in the basic position of the implant. Thus then provides the possibility for two second coupling elements which cooperate with the first coupling elements to approach each other along the spreading direction, for example, in the case where a first coupling element and a second coupling element are mutually supported on one another along the spreading direction. If, of the two coupling elements, one is coupled to a body-side upper supporting element and one to a body-side lower supporting element, this then enables the body-side upper and the body-side lower supporting element to approach each other along the spreading direction.

The spreading of the first coupling elements relative to each other is achieved by means of the fixing device, for example, due to the effect of the previously mentioned first upper stop for an introduction-side upper supporting element as well as the first lower stop for an introduction-side lower supporting element.

In particular, the two first coupling elements are biased relative to each other along the spreading direction.

Preferably, the at least one first coupling element and/or the at least one second coupling element are formed such as to be resiliently deformable, whence more reliable functioning of the coupling device and the implant can then be ensured.

In one advantageous embodiment of the apparatus, it has proved expedient for the at least one first coupling element to be formed as a first carrier which comprises at a free end the introduction-side supporting element and to form a slide-on element which acts along the spreading direction for the at least one second coupling element, and/or for the at least one second coupling element to be formed as a second carrier which comprises at a free end the body-side supporting element and to form a slide-on element which acts along the spreading direction for the at least one first coupling element. When transferring the implant from the introduction position into the spread position, a first coupling element and a second coupling element can slide-on one another and mutually support each other, whereby they each form a slide-on element for the respectively other coupling element. This slide-on feature acts along the spreading direction. The introduction-side supporting element and the body-side supporting element, be it for the upper spinous process or for the lower spinous process, can thereby each be moved along the spreading direction until they can adopt their position in the spread position of the implant. This enables the implant to function in a reliable manner with a simple construction thereof at the same time.

It is of advantage if the surgical apparatus comprises at least one blocking element for preventing a movement of a body-side supporting element along the spreading direction in the introduction position of the implant. This can thereby prevent the at least one body-side upper supporting element and the at least one body-side lower supporting element from increasing their spacing from each other in an unwanted manner in the introduction position of the implant. The insertion depth of the implant before the transfer thereof into the spread position can thus be kept constant. The danger of a body-side supporting element contacting a spinous process or some other body structure in an unwanted manner during the insertion of the implant is thereby reduced.

A simple constructional arrangement of the apparatus is made possible if the at least one blocking element comprises or forms a stop which cooperates with the body-side supporting element or with a carrier incorporating it.

It can be in particular provided that the surgical apparatus comprises more than only one blocking element, wherein by means of each blocking element a movement of a body-side supporting element is preventable along the spreading direction.

A particularly simple constructional arrangement of the apparatus is made possible if the fixing device comprises or forms the at least one blocking element.

Provision may also be made for the at least one blocking element to be arranged to abut the body-side supporting element or a carrier incorporating it in the introduction position of the implant and to be removable from the supporting element or from the carrier before the transfer of the implant from the introduction position into the spread position. The at least one blocking element is only needed after the insertion thereof into the body until such time as the operating surgeon would Like to transfer the implant from the introduction position into the spread position. In this configuration, the at least one blocking element can be arranged to prevent movement of the supporting element on the supporting element or on the carrier. This, for example, defines a blocking position for the at least one blocking element. If the operating surgeon would like to transfer the implant into the spread position, he can remove the at least one blocking element from the supporting element or from the carrier and transfer it into a defined withdrawn position.

It is of advantage if the at least one blocking element is insertable and, in particular, insertable in positively-locking manner into a gap formed between a first carrier incorporating a body-side upper supporting element and a second carrier incorporating a body-side lower supporting element which are spreadable relative to each other along the spreading direction when transferring the implant from the introduction position into the spread position. This thus provides a reliable means for securing the carriers against a spreading movement relative to each other which can be ensured in a simple manner. Consequently, movement of the body-side upper and the body-side lower supporting element relative to each other along the spreading direction can also be prevented.

It is of advantage if the surgical apparatus comprises at least one protection element for the implant, because it can then be protected from damage.

Preferably, the at least one protection element is in the form of a covering which at least partly surrounds the implant on the introduction-side. This thereby provides a means for protecting the implant, particularly on the introduction-side thereof at which an operating surgeon acts, typically using a handling device for the implant or the like. On the other hand, the implant is preferably not surrounded by the covering at the body side of the implant i.e. that region of the implant which is introduced through the inter-vertebral space between the spinous processes. Thus, for inserting the implant into the inter-vertebral space, only a small amount of space is required.

Advantageously, the covering surrounds approximately half of the implant taken with reference to the extent thereof along the clamping direction in order to ensure reliable protection of the implant.

Provision may be made for the covering to at least partly surround the second implant component. This is then arranged e.g. on the introduction-side, whereas the first implant component is arranged on the body side and is moved first into the body.

Preferably, the fixing device comprises or forms the at least one protection element. This makes it possible for the apparatus to have a particularly simple and compact design.

It is of advantage if the fixing device has a substantially U-shaped cross section. In consequence, the fixing device can be given the shape of a clip in the form of a large U. This gives rise to the possibility of forming a protection element for the implant in order to protect it on three sides when the fixing device is attached to the implant.

For the purposes of forming the U-shaped cross section, the fixing device can comprise two segments which are spaced from each other and form the limbs of the U. The segments can be connected at one of their respective ends by means of a connecting segment. At their respective free ends, the first and the second segment can comprise or form the previously described at least one first upper stop, the at least one second upper stop as well as a bone stop element, or they could comprise or form the at least one first lower stop, the at least one second lower stop as well as a bone stop element. A receptacle can be formed in the connecting element for an implant component, and in particular, for the first implant component. The implant component can be introduced at least partly into the receptacle so as to attach the fixing device to the implant.

It is expedient if the fixing device is formed in one piece manner since this simplifies the production thereof.

Preferably, the fixing device is made from a synthetic material because this makes it possible for the fixing device to be produced economically.

In particular, the fixing device can be made from a deformable material. This, for example, gives rise to the possibility of attaching the fixing device to the implant or of detaching it therefrom in a more simple manner.

It is expedient if the fixing device is made from a resiliently deformable material. This is of advantage in particular if the fixing device is to be attached to the implant and is to be deformed thereby. Damage to the fixing device can thereby be prevented.

Provision may be made for the fixing device to be pre-mounted on the implant. This facilitates handling of the apparatus since an operating surgeon does not have to attach the fixing device before the insertion of the implant.

Preferably, a fixing device mounted on the implant is releasable therefrom. After the transfer of the implant from the introduction position into the spread position, the fixing device is no longer needed since the implant abuts the spinous processes as intended. Thus, in this embodiment, this gives rise to the possibility of removing the fixing device from the body after the implant has been inserted.

As an alternative or in addition thereto, provision may be made for the fixing device to be made of an absorbable material so that it is then possible for it to remain in the body after the insertion of the implant into the inter-vertebral space.

It is of advantage, if the fixing device forms at least one first extraction bearing element for extraction of the fixing device from the implant because this then gives rise to the possibility of detaching the fixing device from the implant in a constructionally simple manner. A handling device of the apparatus can grip the first extraction bearing element in order to detach the fixing device from the implant.

It is preferred that the fixing device comprise at least one extraction stop element or that it forms such an element which acts in an extraction direction that is oriented transversely relative to the clamping direction. This permits the fixing device to be stripped from the implant transversely relative to the clamping direction without affecting the positioning of the two implant components relative to each other. In particular, the extraction direction can be oriented perpendicularly to the clamping direction.

It is expedient if the extraction direction is oriented transversely and in particular perpendicularly to the spreading direction. This then gives rise to the possibility of extraction of the fixing device from the implant without inadvertently exerting a force on the upper and/or the lower spinous process that is such as to drive them apart.

It has proved to be expedient for the fixing device to comprise or form a first spreading bearing element for transferring the implant from the introduction position into the spread position. This permits the apparatus to be of a more compact design. A spreading force acting along the clamping direction can be applied to the first spreading bearing element for spreading the implant.

Preferably, the fixing device comprises at least one spreading stop element or forms such an element which acts along the clamping direction. This thus gives rise to the possibility of the fixing device forming a spreading bearing element in a simple constructional manner. For example, a handling device of the apparatus can grip said spreading bearing element for, spreading the implant.

It is expedient if the at least one spreading stop element is coupled to a receptacle formed by the fixing device, in which said receptacle a, and preferably the first, implant component is held. The spreading stop element is coupled by means of the receptacle in force-locking and/or positively-locking manner for example. A spreading force applied to the spreading stop element can thus be transferred to the receptacle and consequently to the implant component, and in particular, to the first implant component that is held therein. For this purpose, the receptacle preferably comprises a stop for the implant component which acts along the clamping direction.

Preferably, the previously mentioned covering forms a coupling element which couples the first spreading bearing element to the receptacle, wherein the latter and the at least one spreading bearing element are formed or comprised by the covering.

Advantageously, the surgical apparatus has a holding device which comprises a receptacle for an implant component and in particular the second implant component, in which said receptacle said component is partially held. The implant component and in particular the second implant component and thus also the implant can be held by means of the holding device.

As an alternative or in addition thereto, provision may be made for the implant and preferably the second implant component to comprise or form a receptacle in which the holding device is held.

It is preferred that the holding device form a second spreading bearing element for transferring the implant from the introduction position into the spread position. If a spreading force acting along the clamping direction is applied to the holding device, the implant can be transferred thereby into the spread position. The counteracting force necessary for this purpose can be applied, as previously mentioned, to the fixing device.

It is of advantage if the fixing device forms a guiding element for the holding device when transferring the implant from the introduction position into the spread position. This thus gives rise to the possibility of moving the holding device in a clearly defined direction relative to the fixing device and hence reliably transferring the implant into the spread position.

In principle, it is possible for an operating surgeon to operate the holding device alone in order to insert the implant into the body. For this purpose, the holding device can comprise or form a gripping element for example.

Preferably however, the holding device comprises a connecting device for the purposes of connection to a first handling device of the surgical apparatus for the implant. This then gives rise to the possibility of connecting the holding device to the first handling device. The holding device can thereby form to a certain extent an intermediate piece between the handling device and the implant. This is of advantage if the holding device is a disposable part which is used with only one implant, whereas the first handling device is a tool which can be used several times.

It is expedient if the connecting device is in the form of a latching device, because this then gives rise to the possibility of connecting the handling device to the holding device in a simple manner. The latching connection between the holding device and the handling device can be releasable.

Preferably, the implant has a locking device comprising a locking element, wherein, in the spread position of the implant, said locking element is transferable in a locking direction that is oriented transversely relative to the clamping direction from a release position, in which the second implant component is movable relative to the first implant component along the clamping direction, into a locking position, in which the second implant component is locked to the first implant component to prevent movement in a direction that is opposed to the clamping direction. It can be ensured by means of the locking element that the two implant components do not move relative to each other along the clamping direction in the spread position of the implant. The implant thereby maintains the spread position after being inserted into the body and can be effective for reliably supporting the spinous processes relative to each other.

Advantageously, the locking element is held in the receptacle together with a fixing element comprised by the second implant component and cooperating with the locking element for locking the implant. Reliable relative positioning of the locking element and the fixing element relative to each other can thus be ensured. This is of advantage both for transferring the locking element from the release position into the locking position and when spreading the implant.

Preferably, the holding device comprises at least one first coupling member or forms such a member which cooperates with at least one second coupling member that is comprised or formed by the locking element for transferring the locking element from the release position into the locking position. Thereby, the holding device can exercise a further function over and beyond the function of holding and possibly also spreading the implant. The at least one first coupling member couples with the at least one second coupling member of the locking element so that it can be transferred into the locking position by means of the holding device. This facilitates the handling of the apparatus.

In the case of a simple constructional embodiment of the apparatus, the at least one first coupling member is in the form of a driver stop for the locking element which acts along the locking direction. In corresponding manner, the at least one second coupling member is in the form of a stop which cooperates with the driver stop. If the holding device is subjected to a force operative in the locking direction, the coupling members couple together so that the locking element can be transferred into the locking position.

It is expedient if, in the locking position of the locking element, the holding device is withdrawable from the implant in the locking direction. When the implant is locked, the holding device is no longer needed. In this embodiment of the implant, it can be withdrawn in the locking direction, for example by continuing to be subjected to a force operative in the locking direction following the locking of the implant.

Expediently, the receptacle comprises an opening through which the fixing element and the locking element are removable from the receptacle in the locking position of the locking element. For example, the opening defines a cross-sectional area that is oriented transversely and in particular perpendicularly to the locking direction through which the fixing element and the locking element can be removed from the receptacle. This permits the holding device to be withdrawn from the implant and the fixing element and the locking element remain on the locked implant.

Expediently, the at least one coupling member of the holding device is arranged at an edge of the opening.

It is preferred that the locking direction should have a parallel component to an extraction direction for the fixing device from the implant, and in particular, the locking direction is oriented in parallel with the extraction direction. This permits both the fixing device and the holding device to be withdrawn from the implant in the same direction—expediently, perpendicularly to the clamping direction and perpendicularly to the spreading direction.

It is of advantage if the holding device is pre-mounted on the implant as this then facilitates the handling of the apparatus by an operating surgeon.

Provision may also be made for the holding device to be attachable to the implant. To this end for example, provision may be made for the previously mentioned receptacle to be expandable so that the fixing element and the locking element can be introduced into the receptacle in order to attach the implant to the holding device.

The holding device is preferably a component of the implant and is comprised thereby, especially if it is pre-mounted on the implant.

It is also possible however, for the holding device to be a component of a first handling device that is to be described hereinafter and is comprised thereby, especially if it is attachable to the implant.

For achieving a simple construction of the holding device, it is expedient if it is formed in one piece manner.

The surgical apparatus may have a first handling device. In particular, it is expedient if the surgical apparatus comprises a first handling device having a gripping element for holding the implant. The operating surgeon can grasp the gripping element in a user friendly manner in order to insert the implant into the body.

The present invention also relates to surgical apparatus with a handling device for holding an implant. Surgical apparatus having a handling device for holding an implant can itself represent an aspect of the present invention if the handling device has a gripping element. It provides user friendly handling of the handling device and thus of the implant for an operating surgeon, in that he acts on the gripping element.

In principle, provision may be made for the implant to be held directly by means of the first handling device.

It is however also possible for the first handling device to comprise a connecting device for connecting to a holding device for the implant. Expediently in this connection, the connecting device is the previously described holding device for the implant on which, for its part, the implant and in particular the second implant component are held.

The connecting device is expediently in the form of a latching device, especially a releasable latching device, in order to facilitate connection of the first handling device to the holding device by an operating surgeon as well as enabling the release thereof if necessary.

In a simple constructional embodiment, the first handling device is in the form of a longitudinally extending gripper arm. The longitudinal extent of the gripper arm provides the operating surgeon with a user friendly means for inserting the implant into the inter-vertebral space.

Advantageously, the surgical apparatus comprises a second handling device for the implant which is movable relative to the first handling device and cooperates therewith for transferring the implant from the introduction position into the spread position. This offers the operating surgeon the possibility of spreading the implant by his grip on the first and the second handling device.

Preferably, the second handling device is transferable relative to the first handling device from a first position into a second position, wherein an end of the second handling device has a differing spacing in the first position than in the second position along the clamping direction relative to an end of the first handling device holding the implant. If the end of the second handling device impinges on the implant when transferring from the first position into the second position, there can thereby be applied to the implant a spreading force, the requisite counteracting force to which can be fed to the implant by the first handling device.

For achieving a reliable relative movement of the second handling device and the first handling device relative to each other, it is of advantage if the second handling device is mounted on the first handling device in movable manner.

It has in practice proved to be particularly expedient, if the second handling device is mounted on the first handling device such as to be pivotal about a pivotal axis oriented transversely relative to the clamping direction. This permits the apparatus to be of a simple construction.

A particularly simple construction of the apparatus is attainable if the second handling device is in the form of pivoted lever.

It is of advantage if the second handling device comprises or forms at least one second spreading stop element which cooperates with at least one first spreading stop element that is preferably comprised or formed by the fixing device when transferring the implant from the introduction position into the spread position. The at least one second spreading stop element, which is arranged expediently on the end of the second handling device, can abut the at least one first spreading stop element. When transferring the second handling device from the first position into the second position, a force acting along the clamping direction can thereby be exerted on the implant and in particular, on the fixing device.

It is expedient if the second handling device comprises or forms at least one second extraction stop element which cooperates with at least one first extraction stop element comprised or formed by the fixing device for extracting the fixing device from the implant. A force effective along the extraction direction can thus be exerted by the second handling device on the fixing device and it can be withdrawn from the implant thereby. A requisite counter-acting force for this process can, for example, be exerted on the implant by a third handling device of the apparatus which is described below.

For example, the at least one second extraction stop element is arranged on the end of the second handling device.

As an alternative or in addition thereto, provision may be made for the at least one extraction stop element not to be formed or comprised by the second handling device. For this purpose for example, the apparatus may then comprise a separate extraction device with the at least one second extraction stop element which is formed separately from the second handling device.

Preferably, the surgical apparatus comprises a barring device having a first barring element comprised by the first handling device and a second barring element comprised by the second handling device, which, relative to each other, are transferable from a disabling position, in which the first barring element and the second barring element cooperate for disabling a movement of the second handling device relative to the first handling device, into a freeing position, in which the first barring element and the second barring element do not cooperate and the second handling device is movable relative to the first handling device, and vice versa. It can be ensured by means of the barring device that the first and the second handling device do not move relative to each other in an unwanted manner. If the implant is introduced into the inter-vertebral space, the first and the second barring element expediently adopt the disabling position. This can thereby prevent the implant spreading in an unwanted manner. It is only by a conscious action on the part of the operating surgeon who transfers the first and the second barring element into the freeing position that the second handling device can be moved relative to the first handling device and thereby spread the implant, i.e. be transferred from the introduction position into the spread position.

Preferably, the first barring element and the second barring element are biased relative to each other in the freeing position with reference to the disabling position thereof. This thus gives rise to the possibility that, to a certain extent, the disabling position forms a basic or resting position of the barring elements. The barring elements can adopt the disabling position whenever the operating surgeon does not consciously transfer them into the freeing position thereof or holds them in this position. This is particularly advantageous when transferring the implant from the introduction position into the spread position, because the implant is typically spread in several small steps. The operating surgeon can thus gradually spread the implant by holding the barring elements in the freeing position, whereafter however, they yield against the bias to such an extent that they adopt their disabling position.

The implant is thereby safeguarded from spreading apart with each spreading step. This facilitates the handling of the apparatus.

In a constructionally simple embodiment of the barring device, it is of advantage if it forms a latching pawl.

In particular, provision may be made for one barring element, the first barring element for example, to be in the form of a latching bar and for one barring element, the second barring element for example, to be in the form of a latching lever. The latching bar can latch together with the latching lever in a plurality of latching positions. This thus gives rise to the possibility that the second handling device can be secured relative to the first handling device in a plurality of positions which are each linked to a different degree of spreading of the implant. At the same time, the latching lever could be an actuating lever of the second handling device.

For biasing the barring elements relative to each other, the barring device expediently comprises at least one resilient element, in the form of a spring for example. This can apply a sort of latching force to the second barring element which the operating surgeon has to overcome in order to transfer the barring elements from the locking position into the freeing position.

It is of advantage if the surgical apparatus comprises an indicator device for indicating the relative position of the first handling device and the second handling device. The operating surgeon can determine the extent to which the implant has spread apart with the aid of the indicator device. Provision may be made for the indicator device to be calibrated in such a way that the absolute spacing of the upper and the lower supporting surface from each other is perceptible by an operating surgeon.

It has in practice proved expedient for the indicator device to be arranged on the barring device. It is thereby readily perceptible to an operating surgeon.

It is preferred that the surgical apparatus comprise a third handling device for the implant which is configured such as to be movable relative to the first handling device and which cooperates with the implant for extracting the fixing device and/or a holding device or the first handling device from the implant in the spread position thereof. As mentioned previously for example, a force can be exerted on the implant by means of the third handling device which works as a counter-acting force to an extraction force for extracting the fixing device from the implant. In corresponding manner, the counter-acting force can become effective for extracting the holding device or possibly, a first handling device that is directly holding the implant, from the implant. This enables the apparatus to be handled in a simple manner.

Advantageously, the third handling device is transferable relative to the first handling device from a withdrawn position into a placement position, wherein at least one counter-stop element comprised or formed by the third handling device is spaced from the implant in the withdrawn position and abuts it in the placement position. After the spreading of the implant, this then gives rise to the possibility of transferring the third handling device relative to the first handling device, upon which the implant is held, in the direction of the implant from the withdrawn position into the placement position. In the placement position, the at least one counter-stop element can abut the implant. In consequence, the previously mentioned counter-acting force for extracting the fixing device and/or the holding device or possibly the first holding device from the implant can be exerted.

In particular, the at least one counter-stop element can be arranged on the end of the third handling device.

Preferably, the third handling device is mounted on the first handling device in movable manner. This enables the third handling device to be transferred from the withdrawn position into the placement position in a reliable manner.

In practice, the process of transferring the third handling device has proved to be particularly reliable if the third handling device is mounted on the first handling device in displaceable manner along a direction oriented in parallel with the extraction direction of the fixing device from the implant and/or parallel to the locking direction of the locking element.

In a particularly simple constructional embodiment, the third handling device is in the form of a slider.

It is of advantage, if the third handling device comprises a first segment with a counter-stop element as well as a second segment with a counter-stop element and if the counter-stop element of the first segment is spaced from the counter-stop element of the second segment along the clamping direction. In the placement position, the first segment and the second segment can thereby abut the implant each with a counter-stop element on this side of and that side of a connecting region of the first handling device to the implant. Taken with reference to the clamping direction, the connecting region is arranged between the counter-stop elements. If a tensile force directed away from the implant is applied to the first handling device, the first handling device or the holding device can then be freed from the implant in a reliable manner without wedging or jamming.

In particular in the placement position, the counter-stop elements of the first segment and the second segment can abut the implant laterally beside the holding device for the implant, taken with reference to the clamping direction. It has been shown in practice, that the holding device can thereby be extracted from the implant in a particularly reliable manner.

If, as previously described, the third handling device is in the form of a slider, it can embrace the first handling device for example, wherein the first and the second segment are arranged on mutually remote sides of the first handling device and/or the holding device.

It is of advantage, if the third handling device forms at least one blocking element for preventing a movement of a body-side supporting element along the spreading direction in the introduction position of the implant, which said at least one blocking element is arranged to abut the body-side supporting element or on a carrier incorporating it in the introduction position, whereby the third handling device adopts a blocking position. Thus, as previously described, the third handling device can be set in a blocking position for blocking the body-side supporting element before the process of spreading the implant and can therefore exercise an additional function.

In the blocking position for example, the at least one blocking element can engage in a gap between two carriers which each comprise a body-side supporting element and which with transferring the implant from the introduction position into the spread position along the spreading direction are spreadable relative to each other, in order to block the movement of the supporting elements relative to each other.

It is expedient if, in the introduction position of the implant, the third handling device is transferable from the withdrawn position into the blocking position and vice versa. This makes it possible for the at least one blocking element to abut the body-side supporting element or its carrier by transferring the third handling device from the withdrawn position into the blocking position before the insertion of the implant into the body. Prior to the spreading apart of the implant, the third handling device can be transferred back into the withdrawn position and the at least one blocking element can be moved such as to be spaced from the implant.

Provision may be made for the at least one blocking element to be formed at an end of the third handling device and in particular its second segment, or for it to be comprised thereby.

Furthermore, provision may be made for the first segment to be configured such as to be movable relative to the second segment and for the first segment and the second segment, for transferring the third handling device from the withdrawn position into the blocking position and vice versa and/or from the withdrawn position into the placement position, to couple in each case by means of coupling elements which cooperate in pairs and are comprised or formed by the first segment and the second segment. In this connection, the coupling elements form cooperating stop elements for example, and in particular, driver stop elements.

Furthermore, due to the effect of the placement of the second segment on the implant in the placement position, provision may be made for the coupling elements effecting the coupling between the first segment and the second segment for transferring the third handling device from the withdrawn position into the blocking position to be decoupled from each other. This permits a relative movement of the first segment and the second segment to be obtained when the second segment reaches the placement position. The first segment can then be moved relative to the second segment until such time as the segments re-couple due to the effect of the cooperating coupling elements in order to apply a force to the implant via both segments.

A first preferred exemplary embodiment of the invention of surgical apparatus 10 that is shown partly in FIG. 4 in the form of an exploded illustration comprises an implant 12, a fixing device 14, a holding device 16 as well as furthermore, a first, a second and also a third handling device 18, 20 or 22 for the implant 12, the fixing device 14 and the holding device 16.

The implant 12 is an inter-vertebral implant for mutually supporting an upper spinous process 24 of a first vertebral body 25 and a lower spinous process 26 of a lower vertebral body 27. It belongs to a class of inter-vertebral implants that is described in DE 20 2008 009 344 U1.

As is clear particularly from FIGS. 1 and 3, the implant 12 comprises a first implant component 28 and also a second implant component 29 which is substantially identical to the first component. The first implant component 28 comprises a first supporting segment 30 which comprise two supporting arms 31 and 32, and also a second supporting segment 33 which comprises a supporting arm 34 that is arranged between the first supporting arm 31 and the second supporting arm 32. The supporting segments 30 and 33 are each formed from a resiliently deformable material and are held together at a first end side 35 of the implant 12 by means of a holding member 36 in the form of a C-shaped clip 37.

In corresponding manner, the second implant component 29 comprises a first supporting segment 38 with two mutually spaced supporting arms 39 and 40 and also a second supporting segment 41 with a supporting arm 42 that is arranged between the supporting arms 39 and 40. The supporting segments 38 and 41 are likewise formed from a resiliently deformable material, and they are held together at an end side 43 of the implant 12 located opposite the end side 35 by means of a holding member 44 in the form of a C-shaped clip 45.

The implant components 28 and 29 are configured such as to be mirror symmetrical relative to each other with respect to a centre of symmetry that is not illustrated in the drawing. The consequence of this is that the supporting arms 31 and 39, the supporting arms 32 and 40 and also the supporting arms 34 and 42 can abut against each other.

Two clamping elements 46 and 47 fixed to the clip 37 extend up to the end side 43 from the end side 35. They thus pass through the implant 12 along its longitudinal extent. At the end side 43, they are connected by means of a connecting member 48. The direction in which the clamping elements 46 and 47 extend defines a clamping direction 49 of the implant 12 and together, the clamping elements 46 and 47 form a tie rod 50 of the implant 12.

In principle, starting from a basic position illustrated in FIG. 2A in which the clip 45 is arranged near the connecting member 48, it is possible to transfer the implant 12 into a spread position that is illustrated in FIGS. 6, 7 and 13 for example by applying force seating to the clip 45 for example along the clamping direction 49. This is effected by displacing the second implant component 29 relative to the first implant component 28 along the tie rod 50. Hereby, the supporting arms 31 and 39 each form respective slide-on elements for each other, the supporting arms 32 and 40 form slide-on elements for each other, and the supporting arms 34 and 42 form slide-on elements for each other. This means that the supporting arms 31 and 39 support one another and slide along each other. In a corresponding manner, the supporting arms 32 and 40 and also the supporting arms 34 and 42 support one another and slide along each other. The implant 12 thereby spreads apart in a spreading direction 51 oriented perpendicularly with respect to the clamping direction 49.

In the spread position of the implant 12, an upper supporting surface 53 for the upper spinous process 24 that is formed by the supporting arms 39, 40 and 34 and also a lower supporting surface 54 for the lower spinous process 26 that is formed by the supporting arms 31, 32 and 42 are at a greater spacing from each other than in the basic position. This then gives rise to the possibility of mutually supporting the spinous processes 24 and 26.

At the free ends thereof, each of the supporting arms 31 and 32 comprises a respective supporting element 55 and 56, these being referred to as "introduction-side" lower supporting elements for reasons that will become evident hereinafter. The supporting arm 34 comprises an introduction-side upper supporting element 57 at the free end thereof. In a corresponding manner, each of the supporting arms 39 and 40 comprises at the free ends thereof a respective supporting element 58 and 59, these being referred to as "body-side" upper supporting elements hereinafter. The supporting arm 42 comprises a body-side lower supporting element 60 at its free end. The supporting arms 31, 32, 34, 39, 40 and 42 thus form carriers for the supporting elements 55, 56, 57, 58, 59 and 60.

In the spread position of the implant 12, the introduction-side supporting elements 55, 56 and 57 can laterally support the spinous processes 26 and 24 and for this purpose for example, abut thereon, namely on those sides of the spinous processes 24 and 26 which face a point of entry into the human body through which the implant 12 is inserted into the body (FIGS. 6, 7 and 13).

In corresponding manner, in the spread position of the implant 12, the body-side upper supporting elements 58, 59 and 60 can laterally support the spinous processes 24 and 26 and for this purpose for example, abut thereon, namely on the body side, i.e. on those sides of the spinous processes 24 and 26 which are remote from a point of entry for the implant 12.

In the basic position of the implant (FIG. 2A), the introduction-side upper supporting element 57 is spaced from the introduction-side lower supporting elements 55 and 56 by a spacing $d_G$ along the spreading direction 51, which is identical to the spacing of the body-side lower supporting element 60 from the body-side upper supporting elements 58 and 59 along the spreading direction 51. This spacing $d_G$ defines the insertion depth of the implant 12 in its basic position, and it must, in particular, be smaller than the spacing of the spinous processes 24 and 26 from each other so that the implant 12 can be introduced into the inter-vertebral space.

In order to move the implant 12 out of the basic position into the preferred introduction position for inserting it into the body, the apparatus 10 comprises the previously mentioned fixing device 14. The fixing device 14 is in the form of a covering 61 having a substantially U-shaped cross section. Hereby, the covering 61 comprises a first segment 62 and also a second segment 63 that is spaced therefrom, said segments being connected to one another at one of their ends by a third segment 64.

At the third segment 64 and partially bounded thereby, the covering 61 comprises a first receptacle 65 into which the connecting member 48 can be introduced through an introduction opening 66. The first receptacle 65 is dimensioned such that the connecting member 48 can be placed in positively-locking manner in the receptacle. This then gives rise to the possibility of connecting the connecting member 48 and thus the first implant component 28 and thus in turn, the implant 12 to the covering 61, or, differently expressed, of attaching the covering 61 to the implant 12. The connecting member 48 is in engagement with the third segment 64 in the receptacle 65.

Laterally, beside the first receptacle 65, the covering 61 comprises a second receptacle 67 which is bounded on the upper side by the first segment 62 and on the lower side by the second segment 63. The second implant component 29 can be introduced into the second receptacle 67 through an introduction opening 68 up to approximately half the longitudinal extent thereof taken with respect to the spacing of the clip 45 from the supporting elements 58 to 60. The walls of the second receptacle 67, which are formed by the first and by the second segment 62 and 63 and face the second implant component 29, are adapted to the contour of the supporting segments 41 and 38. The second implant component 29 can thus be placed virtually in positively-locking manner in the second receptacle 67 along the spreading direction 51. The covering 61 is also held on the second implant component 29 thereby.

At the free end 69 thereof remote from the third segment 64, the first segment 62 comprises a first upper stop element 70 which is effective for the supporting arm 34 in a direction opposed to the spreading direction 51, and also a second upper stop element 71 which is effective for the supporting arm 34 in the spreading direction 51. In corresponding manner, the second segment 63 comprises at the free end 72 thereof remote from the third segment 64 a first lower stop element 73 for the supporting arms 31 and 32 which acts in a direction opposed to the spreading direction 51 and also a second lower stop element 74 (FIG. 2B) which is effective for the supporting arms 31 and 32 in the spreading direction 51.

The lengths of the segments 62 and 63 are dimensioned such that, if the covering 61 is attached to the implant 12, the supporting arms 31 and 32 are then spread apart relative to the supporting arm 34 along the spreading direction 51 compared with the basic position. In particular, the supporting arms 31 and 32 on the one hand and the supporting arm 34 on the other are biased relative to each other. In this way, the supporting arms 31 and 32 and the supporting arm 34 are spread apart relative to each other in a manner such as also occurs when transferring the implant 12 from the basic position into the spread position.

The supporting arm 34 is supported on the first upper stop element 70 by means of the introduction-side upper supporting element 57, and the supporting arms 31 and 32 are supported on the first lower stop element 73 by means of the introduction-side lower supporting elements 55 and 56 in order to ensure the previously described spreading of the supporting arms 32 and 33 relative to the supporting arm 34.

This defines an introduction position of the implant 12 in which the introduction-side upper supporting element 57 has a spacing $d_{EE}$ from the introduction-side lower supporting elements 55 and 56 which is greater than the spacing $d_G$ of the same supporting elements 57 on the one hand and 55, 56 on the other from each other in the basic position of the implant 12.

The consequence of this is that, when inserting the implant 12 into the inter-vertebral space, the introduction-side supporting elements 55, 56 and 57 form stops for the lower spinous process 26 and the upper spinous process 24. This makes it easier for an operating surgeon to introduce the implant into the inter-vertebral space because it enables the correct positioning of the implant 12 relative to the spinous processes 24 and 26 to be effected. In particular, this can also prevent the implant 12 from being inserted too far into the inter-vertebral space. This then gives rise to the possibility of reducing the danger of injury to the patient.

The introduction-side supporting elements 55 and 56 on the one hand and also 57 on the other can additionally abut the second lower stop element 74 and the second upper stop element 71 in the introduction position of the implant 12. This provides for a yet more reliable attachment of the covering 61 to the implant 12 and moreover, prevents excessive spreading of the supporting arms 31 and 32 relative to the supporting arm 34 and thus the danger of causing damage to the implant 12.

Furthermore, the covering 61 comprises two bone stop elements 75 and 76 which are formed at the free end 69 of the first segment 62 and the free end 72 of the second segment 63. The bone stop elements 75 and 76 form stops for the spinous processes 24 and 26 in addition to the introduction-side supporting elements 55 to 57.

As previously mentioned, the supporting arms 31, 32 and 34 of the first implant component form slide-on elements for the supporting arms 39, 40 and 42 of the second implant component 29 and vice versa. Due to the fact that the supporting arms 31 and 32 are spread relative to the supporting arm 34 along the spreading direction 51, 40 in the introduction position of the implant 12, the supporting arms 39 and 41 on the one hand and the supporting arm 42 on the other move towards one another along the spreading direction 51 in the introduction position as a result of the resilient nature of the supporting segments 38. Consequently, the supporting arms 31 and 39, the supporting arms 32 and 40 and also the supporting arms 34 and 42 abut even in the introduction position of the implant 12.

The consequence of this, however, is that the spacing of the body-side lower supporting element 60 from the body-side upper supporting elements 58 and 59 is reduced in the introduction position of the implant 12, where it amounts to $d_{EK}$, relative to the spacing $d_G$. The spacing $d_{EK}$ thus defines the insertion depth of the implant 12 in the introduction position which is smaller than the insertion depth $d_G$ of the implant 12 in the basic position. When inserting the implant 12 into the inter-vertebral space, there is then a lesser danger of an operating surgeon inadvertently knocking against the spinous processes 24 and 26 or else other body structures such as tendons, ligaments or muscles for example. The danger of injury to the patient is reducible thereby when inserting the implant 12 in the introduction position.

Due to the spreading of the supporting arms 31 and 32 relative to the supporting arm 34 in the introduction position of the implant 12 by means of the fixing device 14, the supporting arms 39 and 40 approach the supporting arm 42 along the spreading direction automatically so to speak as previously described. The implant 12 thus forms a coupling device 77 in which the supporting arms 31 and 39, 32 and 40 and also 34 and 42 are respectively coupled to one another. The supporting arms 31, 32 and 34 with the introduction-side supporting elements 55, 56 and 57 are also referred to as first coupling elements 78, 79 and 80 of the coupling device 77. In corresponding manner, the supporting arms 39, 40 and 42 are referred to as second coupling elements 81, 82 and 83 of the coupling device 77.

In order to prevent the second implant component 29 from spreading in an unwanted manner when inserting it into the body and the supporting arms 39 and 40 from moving relative to the supporting arm 42 along the spreading direction 51, the covering 41 comprises a blocking element 84 for the supporting arm 39, a blocking element 85 for the supporting arm 42 and also a blocking element for the supporting arm 40 which is not illustrated in the drawing (FIG. 2B). The blocking element 84 is arranged on the first segment 62 at an edge of the second receptacle 67, and it can cooperate with an introduction-side upper supporting element 86 of the supporting arm 39. In corresponding manner, the blocking element 85 arranged is on the second segment 63 at an edge of the second receptacle 67, and it cooperates with an introduction-side lower supporting element of the supporting arm 42.

The covering 61 is formed in one piece manner, and it consists of a resiliently deformable synthetic material. It can already be pre-mounted on the implant 12 prior to delivery. However, it is also possible for the covering 61 to be attached thereto just before the usage of the implant 12.

Due to the fact that the covering 61 surrounds the second implant component 29 on three sides, it forms a protective element for the implant 12.

On the sides of the segments 62 and 63 remote from the second receptacle 67, the covering 61 comprises two wedge-shaped projections 88 and 89. The projections 88 and 89 each form a respective spreading stop element 90 and 91 that is effective along the clamping direction 49. If a spreading force acting along the clamping direction 49 is exerted on the spreading stop elements 90 and 91, it is applied to the connecting member 48 that is held in positively-locking manner in the first receptacle 64 and thus too, to the first implant component 28. The covering 61 with the projections 88 and 89 thus forms a first spreading bearing element 92 or 93 for spreading the implant 12.

Moreover, the projections 88 and 89 comprise a respective extraction stop element 94 and 95 that acts perpendicularly to the clamping direction 49 and also perpendicularly to the spreading direction 51. Acting in this direction, which defines an extraction direction 951 for extraction of the covering 61 from the implant 12 (in FIG. 2B, perpendicularly to the plane of the drawing), the covering 61 can be extracted from the implant 12. In this way, the projections 88 and 89 form a respective extraction bearing element 96 and 97 for extracting the covering 61 from the implant 12.

As is apparent in particular from FIGS. 3, 11 and 12, the implant 12 comprises a locking device 98 having a plate-like locking element 99 which is arranged on the side of the clip 45 facing the end side 43 and defines a plane oriented perpendicularly to the clamping direction 49. The implant 12 can be locked in the spreading direction by means of the locking element 99, in that it is transferred from a release position, in which the second implant component 29 is movable relative to the first implant component 28 along the clamping direction 49, into a locking position. In the locking position of the locking element 99, the second implant component 29 is locked to the first implant component 28 against movement in the direction of the clamping direction 49.

The mechanism for achieving this effect is described in the publication DE 20 2008 009 344 U1 which is incorporated herein. Whereas in the release position (FIG. 11) the locking element 99 is freely movable along the clamping direction 49 relative to the clamping elements 46 and 47 which pass through the through openings 100 and 101 therein, it is engaged between respective locking members in the form of peripheral ribs 102 that are formed on the clamping elements 46 and 47 in the locking position (FIG. 12). The locking element 99 can thereby be supported on the first implant component 28 in the locking position. The second implant component 29 can be supported on the locking element 99 by the clip 45 which forms a fixing element and is thereby secured against movement relative to the first implant component 28.

In the locking position of the locking element 99, the locking element 99 and the clip 45 can additionally engage behind one another by means of securing members in the form of projections 103 on the locking element 99 and projections 104 on the clip 45. The locking element 99 is thereby secured against movement to the second implant component 29 in a direction opposed to the locking direction 105 when in the locking position. The locking direction 105 is oriented perpendicularly to the clamping direction 49 and perpendicularly to the spreading direction 51 and is parallel to the extraction direction 951, and the locking element 99 can be transferred from the release position into the locking position in the locking direction 105.

The securement of the locking element 99 to the second implant component 29 is effected automatically to a certain extent in the locking position. This is due to the fact that the implant components 28 and 29 are biased relative to each other along the clamping direction 49 in the spread position. If the locking element 99 adopts the locking position, it moves thereby relative to the clip 45 along the clamping direction 49, this then leading to automatic engagement behind one another of the clip 45 and the locking element 99 by means of the projections 103 and 104.

The holding device 16 for the implant 12 mentioned hereinabove is in the form of a clip, as is particularly clear from FIGS. 1 and 3. For this purpose, the holding device 16, which is referred to hereinafter as an adapter 106, comprises a first holding element 107 and a second holding element 108. The holding elements 107 and 108 are connected together at an end side 109 of the adapter 106 by a web-like connecting section 110, and they form arms 111 and 112 as it were of the clip-like adapter 106.

At the side opposite the end side 109, the adapter 106 forms a receptacle 113 between the arms 111 and 112, and the clip 45 and the locking element 99 can be arranged in this receptacle. The sides of the arms 111 and 112 facing the clip 45 and the locking element 99 are matched to the contours thereof so that, when the adapter 106 is mounted on the implant 12, the clip 45 and the locking element 99 are arranged in positively-locking manner in the receptacle 113 along the spreading direction 51. The implant 12 can thus be held securely on the adapter 106.

The adapter 106 can be pre-mounted on the implant 12 prior to delivery. It is however also possible for the adapter 106 to be attached to the implant 12 at a later time. To this end, the receptacle 113 can be extended, namely in that the arms 111 and 112 are spread relative to each other along the spreading direction 51. This then gives rise to the possibility of introducing the clip 45 and the locking element 99 into the receptacle 113 through an end-side opening 114 formed therein. The end-side opening 114 is arranged in the end side 115 of the adapter 106 located opposite the end side 109.

The end-side opening 114 is dimensioned along the clamping direction 49 such that the clip 45 and the locking element 99 cannot be removed from the receptacle 113 through the end-side opening 114 so long as the locking element 99 is in the release position and even in the locking position insofar as it is not yet interlocked with the clip 45. At this moment, the locking element 99 and the clip 45 are (still) held in positively-locking manner in the receptacle 113 along the clamping direction 49.

If, however, the locking element 99 and the clip 45 interengage by means of the projections 103 and 104, they can be removed from the receptacle 113 through the end-side opening 114.

Over and above the function of holding the implant 12, the adapter 106 forms a second spreading bearing element 116 for transferring the implant 12 from the introduction position into the spread position. This is because of the fact that it engages the clip 45, consequently the second implant component 29 and thus too the implant 12. If the adapter 106 is subjected to a force acting along the clamping direction 49, the second implant component 29 can be moved relative to the first implant component 28 and the implant can thus be spread.

If the adapter 106 together with the covering 61 is attached to the implant 12, it is arranged in positively-locking manner in the second receptacle 67 formed by the covering 61 along the spreading direction 51. This leads to the fact that the first segment 62 of the covering 61 forms a guiding element 117 for the first arm 111 and the second segment 63 thereof forms a guiding element 118 for the arm 112 (FIG. 2B). This thereby ensures a particularly reliable movement of the adapter 106 relative to the covering 61 and consequently reliable transference of the implant 12 from the introduction position into the spread position.

Moreover, the adapter 106 has yet a further function. It serves for transferring the locking element 99 from the release position into the locking position. For this purpose, the adapter 106 comprises two coupling members 119 and 120 which are respectively formed on the arms 111 and 112 and especially at an edge 121 of the end-side opening 114. The coupling members 119 and 120 are in each case in the form of driver stops 122 and 123. They can cooperate with a further coupling member 124 comprised by the locking element 99 which is formed on the end face of the locking element 99.

If a force is exerted on the adapter 106 in the locking direction 105, the coupling members 119 and 120 are coupled to the coupling member 124. This means that the driver stops 122 and 123 subject the locking element 99 to a force directed in the locking direction 105 so that it can be transferred from the release position into the locking position (FIGS. 11 and 12). In connection therewith, due to the size of the end-side opening 114 along the clamping direction 49, it is ensured that neither the locking element 99 nor the clip 45 depart from the receptacle 113. If the locking element 99 adopts its locking position and if the locking element 99 and the clip 45 engage behind one another by means of the projections 103 and 104, the adapter 106 can nevertheless be extracted from the implant 12 by the application of further force in the locking direction 105. The locking element 99 and the clip 45 can then be removed from the receptacle 113 through the end-side opening 114.

Together with the extraction of the adapter 106 from the implant 12, the latter is thus locked automatically in the spread position as previously described. In addition, the locking element 99 is automatically secured to the clip 45 so that it cannot be transferred back again into the release position. This ensures reliable handling of the implant 12.

At an approximately central position between the end sides 109 and 112, the adapter 106 comprises a connecting device 125 in the form of a latching device 126. This then gives rise to the possibility of connecting the adapter 106 to the first handling device 18 of the apparatus 10 mentioned hereinabove in releasable manner. For its part, the first handling device 18 (FIG. 4) which is in the form of a gripper arm the 127 likewise comprises a connecting device 128 in the form of a latching device 129, which is connectable to the latching device 126 in releasable manner. It is arranged at one end 130 of the gripper arm 127. At the end thereof opposite the end 130, the gripper arm 127 comprises a gripping element 131 which can be grasped by an operating surgeon in a simple manner.

At an approximately central position between the connecting device 128 and the gripping element 131, the gripper arm 127 comprises two bearing elements in the form of bearing journals 132 and 133. The second handling device 20, which is in the form of a pivoted lever 134, is mounted on the gripper arm 127 at the bearing journals 132 and 133 such as to be pivotal about a pivotal axis 135 which is defined by the bearing journals 132 and 133 and is oriented in parallel with the spreading direction 51 and thus perpendicularly to the clamping direction 49.

The pivoted lever 134 is sub-divided on the side thereof facing the implant 12 into two segments 136 and 137 which can accommodate the gripper arm 127 therebetween. The respective ends 138 and 139 of the segments 136 and 137 have a hook-like shape. There, the segments 136 and 137 comprise a respective second spreading stop element 140 and 141 acting along the clamping direction 49. These can cooperate with the first spreading stop elements 90 and 91 on the covering 61 for spreading the implant 12.

In like manner, at their respective ends 138 and 139, the segments 136 and 137 each comprise a second extraction stop element 142 and 143. The latter can cooperate with the first extraction stop elements 95 and 96 of the covering 61 for extracting it from the implant 12.

At the side opposite the ends 138 and 139, the pivoted lever 134 comprises an actuating lever 145 which is pivotal about a pivotal axis 144 which is oriented in parallel with the pivotal axis 135. The actuating lever 145 is in the form of a latching lever 146, and it comprises a latching element 147 in the form of a latching tooth 148 (FIGS. 8A and 8B).

The latching tooth 148 can cooperate with a further latching element 149 in the form of a latching bar 150 held on the gripper arm 127 in order to bar the pivoted lever 134 from pivoting relative to the gripper arm 127 about the pivotal axis 135 or to enable it to do so. For this reason, the latching lever 146 forms a barring element 151, and the latching bar 150 forms a barring element 152. Together, they form a barring device 153 of the apparatus 10.

When the barring elements 151 and 152 are in engagement with one another (FIG. 8B), the pivoted lever 134 cannot be pivoted relative to the gripper arm 127. This defines a barring position of the barring device 153. The barring position is a basic position of the barring device 153, because in this position the latching lever 146 is caused to pivot about the pivotal axis 144 by means of two resilient elements in the form of springs 154 and 155, which are arranged in an end-side receptacle 156 in the pivoted lever 134, so that it automatically comes into engagement with the latching bar 150.

It is only when the operating surgeon presses the latching lever 146 against the resetting force of the springs 154 and 155 that the latching lever 146 and the latching bar 150 disengage (FIG. 8A) and the barring device 153 adopts its freeing position. The pivoted lever 134 can then be pivoted relative to the gripper arm 127.

In order to transfer the barring device 153 from the barring position into the freeing position, it is necessary for the operating surgeon to apply an actuating force along an actuating direction 157 to the latching lever 146, the pivoted lever 134 also being subjected to a force along the actuating direction 157 for spreading the implant 12 relative to the gripper arm 127. This means then, that the implant 12 can only be transferred from the introduction position into the spread position if the operating surgeon transfers the barring device 153 into the freeing position so that the implant 12 is not spread unintentionally.

At the time of insertion of the implant 12 into the body, the barring device 153 already prevents unintentional spreading of the implant 12 by virtue of a counter-pressure that is exerted on the clip 37 by body tissue and is opposed to the introduction direction.

Furthermore, the biasing of the barring elements 151 and 152 relative to each other by the springs 154 and 155 serves to prevent the implant 12 from being transferred back again from the spread position into the introduction position when the implant 12 is spread somewhat and the spinous processes 24 and 26 exert a force on the implant 12. Instead, it remains in the spread position. This facilitates handling of the apparatus by an operating surgeon, because the implant 12 can be spread in step-like manner by the operating surgeon by applying force to the latching lever 146 and the operating surgeon can check to a certain extent after each "spreading step" as to whether the implant 12 is sufficiently spread in order to ensure adequate support of the spinous processes 24 and 26 relative to each other.

The operating surgeon can check as to the position the gripper arm 127 and the pivoted lever 134 have adopted relative to each other by means of an indicator device 158 which comprises a scale 159 and is arranged on the latching bar 150. From this, the operating surgeon can derive the amount by which the implant 12 has already expanded. Provision may be made, in particular, for the scale 159 to be calibrated in such a manner that the spacing of the supporting surfaces 53 and 54 from each other can be read off directly from the scale 159.

A further indicator device 160 incorporating a scale 161 is arranged at the end of the pivoted lever 134. With aid of this scale 161, the operating surgeon can determine the magnitude of the actuating force that he is applying to the latching lever 146 against the resetting force of the springs 154 and 155 in order to spread the implant 12. This actuating force is a measure for the supporting force being triggered by the spinous processes 24 and 26 on the implant 12 and derived via the gripper arm 127 and the pivoted lever 134. The operating surgeon can thus also determine the supporting force with the aid of the scale 161. The scale 161 can be calibrated in the same way as the scale 159.

The third handling device 22 of the apparatus 10 is in the form of a slider 162 which is mounted on the gripper arm 127 such as to be displaceable in parallel with the locking direction 105 and the extraction direction 951. It comprises a first end 163 having an actuating member 164 for the operating surgeon arranged thereon. The slider 162 comprises a second end 165 located opposite the first end 163. At a point located approximately centrally between the ends 163 and 165 and up to the end 165, the slider 162 forms a first segment 166. Furthermore, it forms a second segment 167. These are spaced from each other and they can accommodate the gripper arm 127 therebetween and likewise too, the end of the adapter 106 protruding from the covering 61.

At the end face of the second end 165, the first segment comprises a counter-stop element 168, and in corresponding manner, the end face of the second segment comprises a counter-stop element 169. The counter-stop elements 168 and 169 are referred to as such, because a counter-acting force that is necessary for extracting the covering 61 and the adapter 106 from the implant 12 can be applied to the implant 12 via said elements. This can be effected in a placement position of the slider 162. In the placement position, the counter-stop element 168 abuts the tie rod 50, and in particular, the clamping element 47. The counter-stop element 169 can abut the second implant component 29 in the placement position, and in particular, the supporting segments 38 and 41 (FIG. 9).

In a withdrawn position of the slider 152 into which it can be transferred by being displaced relative to the gripper arm 127, the counter-stop elements 168 and 169 are spaced from the implant 12.

Summarising the previous explanations, the apparatus 10 in accordance with the preferred exemplary embodiment of the invention may function as follows:

The fixing device 14 is attached to the implant 12 in order to move the latter from the basic position into the introduction position. The holding device 16 is attached to the implant 12. These two preliminary steps may already have been effected at the factory. Typically, the holding device 16 and the covering 61 are disposable parts which can be freed from the implant 12 after it has been inserted into the body and they can then be disposed of.

The gripper arm 127 is connected to the adapter 106 by means of the latching devices 126 and 129. The operating surgeon can hold the implant 12 on the gripping element 133 therewith. The pivoted lever 134 can be pivoted relative to the gripper arm 127 in such a way that the segments 136 and 137 slide-on the wedge-shaped projections 88 and 89. The spreading stop elements 90 and 140 and also 91 and 141 can come into contact with one another. In like manner, the extraction stop elements 94 and 142 and also 95 and 143 can come into contact with one another. The slider 162 adopts a withdrawn position.

The implant 12 is safeguarded from spreading apart unintentionally by means of the blocking elements 84 and 85 and also the barring device 153. It can be introduced into the inter-vertebral space by the operating surgeon (FIG. 5). The bone stop elements 75 and 76 and also the introduction-side supporting elements 55, 56 and 57 form stop elements for the spinous processes 24 and 26 and thereby limit the insertion depth of the implant 12 into the inter-vertebral space.

By applying force to the latching lever 146 along the actuation direction 157, the pivoted lever 134 can be pivoted relative to the gripper arm 127. The spreading stop elements 90 and 140 and also 91 and 141 cooperate in order to impose a spreading force on the first implant component 28. The counter-acting force necessary for the spreading process is imposed on the second implant component 29 via the adapter 106 by means of the gripper arm 127. The implant 12 is transferred from the introduction position into the spread position (FIGS. 6 and 7). The spinous processes 24 and 26 are supported relative to each other by means of the respective supporting surfaces 53 and 54.

The operating surgeon can hold and operate the gripper arm 127 and thus the pivoted lever 134 coupled thereto with only one hand. He can transfer the slider 162 on the actuating member 164 from the withdrawn position into the placement position with his other hand. The extraction stop elements 94 and 142 and also 95 and 143 cooperate for extracting the covering 61 from the implant 12. The counter-acting force is imposed on the implant 12 by the counter-stop elements 168 and 169.

At the same time, the adapter 106 can be extracted from the clip 37 and from the locking element 99. The counter-acting force necessary for this action can likewise be imposed on the implant 12 by the counter-stop elements 168 and 169, and the tensile force is applied to the gripper arm 127. When extracting the adapter 106 from the implant 12, the locking element 99 can be transferred from the release position into the locking position as previously described and consequently the implant 12 can be automatically locked (FIGS. 9 to 12). The clip 37 and the locking element 99 can be removed from the receptacle 113 through the end-side opening 114. The covering 61 and the adapter 106 held on the gripper arm 127 and on the pivoted lever 134 can thus be extracted from the implant 12 together (FIG. 13). The locked implant 12 remains in the spread position as intended between the spinous processes 24 and 26.

The adapter 106 and the covering 61 can be freed respectively from the gripper arm 127 and from the pivoted lever 134 and then reused or disposed of.

A second preferred exemplary embodiment in accordance with the invention of surgical apparatus is partly shown in FIG. 16 in the form of an exploded illustration and is there allocated the reference symbol 170. It comprises an implant 172, a fixing device 174, the holding device 16, a first handling device 176 which functions in the same manner as the first handling device 18, the second handling device 20 and also a third handling device 178.

The individual components of the apparatus 170 are for the most part identical to those of the apparatus 10, and the same reference symbols are therefore used for equivalent and functionally equivalent features of the apparatus 10 and 170. The advantages attainable with the apparatus 10 can likewise be obtained with the apparatus 170. Only the essential differences between the individual components of the apparatus 10 and 170 are discussed hereinafter.

Other than was the case for the implant 12, the orientations of the supporting arms 31, 32, 34, 39, 40 and 42 along the spreading direction 51 are reversed in the implant 172. This means that the supporting arms 31 and 32 respectively comprise introduction-side upper supporting elements 179 and 180 and the supporting arm 34 an introduction-side lower supporting element 181. The supporting arms 39 and 40 respectively comprise body-side lower supporting elements 182 and 183, and the supporting arm 42 comprises a body-side upper supporting element 184 (FIGS. 14 to 15B). The supporting arms 31, 32, 34, 39, 40 and 42 thus form carriers for the supporting elements 179, 180, 181, 182, 183 and 184.

Accordingly, in the introduction position of the implant 172, the introduction-side upper supporting elements 179 and 180 abut the upper stop elements 70 and 71 of the fixing device 174, and the introduction-side lower supporting element 181 abuts the lower stop elements 73 and 74 of the fixing device 174.

Other than was the case for the covering 61, the covering 185 formed by the fixing device 174 does not incorporate the bone stop elements 75 and 76.

Likewise, in contrast to the covering 61, the covering 185 does not comprise the blocking elements 84 and 85.

The third handling device 178 is similar to the third handling device 22 and is in the form of a slider 186 having a first segment 187 and a second segment 188. Basically, the segments 187 and 188 are displaceable relative to each other along the gripper arm 127 and can couple to one another in different ways:

As is clear from FIGS. 16 and 17 in particular, the first segment 187 comprises an actuating member 190 at the first end 189 of the slider 186. At the second end 191 thereof which is located opposite the first end 189, the first segment 187 comprises a counter-stop element 192 which is arranged to abut the tie rod 50 in a placement position of the slider 186.

At a point approximately centrally between the ends 189 and 191, the first segment 187 has a projection 193 directed toward the second segment 188. The projection 193 forms two coupling elements 194 and 195 and is in the form of a driver stop 196 or a latching nose 197. These each act along the locking direction 105. At a second end 198 thereof opposite the first end 189, the second segment 188 comprises a pair of counter-stop elements 199 and 200 which are separated from each other by a slit-like gap 201. At a point approximately centrally between the ends 189 and 198, the second segment 188 comprises a projection 202 which forms a coupling element 203 in the form of a counter-stop 204 for the driver stop 196. Moreover, the second segment 188 comprises a coupling element 205 in the form of a projection 206 for the latching nose 197 which is close to the projection 202. Furthermore, the second segment 188 forms a coupling element 207 in the form of a shoulder 208 which can cooperate with the actuating member 290.

For introducing the implant 172 into the body in the case of the apparatus 170, the gripper arm 127 is firstly fixed to the adapter 106 and the pivoted lever 134 is adapted to the covering 185 (FIG. 17, in which the pivoted lever 134 is not illustrated). The slider 186 adopts a withdrawn position in which the counter-stop elements 192, 199 and 200 are spaced from the implant 172 and the latching nose 197 abuts the projection 206.

Before introducing the implant 172 into the body, the slider 186 is subjected to a force which is directed toward the implant 172 and is applied by the operating surgeon via the actuating member 190. The segments 187 and 188 couple by means of the latching nose 197 and the projection 206. This permits the counter-stop elements 199 and 200 to be fed into a gap 209 which is formed between the supporting segments 38 and 41 of the implant 172 (FIGS. 15A and 15B). The clamping elements 46 and 47 thereby engage in the gap 201 between the counter-stop elements 199 and 200 (FIGS. 18 and 19).

The second segment 188 is adapted to fit in positively-locking manner against the counter-stop elements 199 and 200 in the gap 209 so that the supporting arms 39 and 40 cannot be spread relative to the supporting arm 42 along the spreading direction 51. For this reason, the counter-stop elements 199 and 200 form respective blocking elements 210 and 211 with the aid of which unwanted spreading of the implant 172 can be prevented. This is also a result of the fact that the adapter 106 is prevented from making a movement relative to the covering 185 due to the positive-fitting engagement of the second segment 188 in the gap 209. The position of the slider 186 wherein the second segment 188 engages in the gap 209 is referred to as the blocking position of the slider 186.

For spreading the implant 172 after it has been introduced into the inter-vertebral space, the operating surgeon must subject the actuating member 190 to a force directed in the locking direction 105. The segments 187 and 188 are thereby coupled by means of the driver stop 196 and the counter-stop 204. The slider 186 can thus be transferred once more into the withdrawn position. Thereupon, the implant 172 can be transferred from the introduction position into the spread position in a manner corresponding to the previously described way for the implant 12 (FIG. 20).

In order to free the covering 185 and the adapter 106 from the implant 172 after the spreading thereof, the operating surgeon can again subject the actuating member 190 to a force directed toward the implant 172. This leads to the second segment 188 with the counter-stop elements 199 and 200 coming into contact with the second implant component 29 upon which it is then supported. The latching nose 197 can decouple from the projection 206 due to the effect of the actuating force applied by the operating surgeon and the counter-acting force of the implant 172. The first segment 187 can thus be displaced relative to the second segment 188 along the gripper arm 127 until such time as the actuating member 190 comes into contact with the shoulder 208 (FIG. 21). When this is the case, the counter-stop element 192 of the first segment 187 abuts the clamping element 47.

The shoulder 208 forms a driver stop 212 so that a counter-acting force for extracting the covering 185 and the adapter 106 can be applied to the implant 172 by continuing to subject the actuating member 190 to a force directed towards the implant. As a result, in the case of the apparatus 170, the covering 185 and the adapter 106 can be extracted from the implant 172 and furthermore, the latter automatically locked, as was previously described for the case of the apparatus 10.

The invention claimed is:

1. A surgical apparatus comprising an implant for mutually supporting an upper spinous process of a first vertebral body by means of an upper supporting surface and a lower spinous process of a second vertebral body by means of a lower supporting surface,
    wherein the implant comprises a first implant component and a second implant component which is configured such as to be movable relative thereto along a clamping direction in order to transfer the implant out of a basic position in a spreading direction that is oriented transversely relative to the clamping direction into a spread position in which the upper supporting surface and the lower supporting surface are a greater spacing from each other than in the basic position,
    and wherein the implant comprises at least one introduction-side upper supporting element and at least one introduction-side lower supporting element that are used for laterally supporting the upper spinous process and the lower spinous process on the introduction-side, respectively, in the spread position of the implant,
    wherein the apparatus comprises a fixing device for the implant that is used for spreading the at least one introduction-side upper supporting element and the at least one introduction-side lower supporting element relative to each other along the spreading direction and by means of which fixing device the implant is movable from the basic position into an introduction position in which the at least one introduction-side upper supporting element and the at least one introduction-side lower supporting element are at a greater spacing relative to each other than in the basic position, and from which the implant is transferable into the spread position by moving the second implant component relative to the first implant component along the clamping direction,
    wherein the implant comprises at least one body-side upper supporting element and at least one body-side lower supporting element for laterally supporting of the upper spinous process and the lower spinous process on the body-side, respectively, in the spread position of the implant, and
    wherein the surgical apparatus comprises a coupling device having at least one first coupling element which is coupled to an introduction-side supporting element and also at least one second coupling element which is coupled to a body-side supporting element and which, in the introduction position of the implant, cooperates with the at least one first coupling element for decreasing the spacing of the at least one body-side upper supporting element and the at least one body-side lower supporting element from each other relative to their spacing from each other in the basic position of the implant.

2. A surgical apparatus in accordance with claim 1, wherein the fixing device comprises or forms at least one of an at least one first upper stop that acts in a direction opposed to the spreading direction for the at least one introduction-side upper supporting element or a carrier incorporating it and an at least one first lower stop that acts in a direction opposed to the spreading direction for the at least one introduction-side lower supporting element or a carrier incorporating it.

3. A surgical apparatus in accordance with claim 1, wherein the fixing device comprises or forms at least one of an at least one second upper stop which acts in the spreading direction for the at least one introduction-side upper supporting element or a carrier incorporating it and an at least one second lower stop which acts in the spreading direction for the at least one introduction-side lower supporting element or a carrier incorporating it.

4. A surgical apparatus in accordance with claim 1, wherein the fixing device comprises or forms at least one of an at least one introduction-side upper bone stop element for the upper spinous process and an at least one introduction-side lower bone stop element for the lower spinous process.

5. A surgical apparatus in accordance with claim 1, wherein the first implant component comprises the at least one introduction-side upper supporting element and the at least one introduction-side lower supporting element.

6. A surgical apparatus in accordance with claim 1, wherein the second implant component comprises the at least one body-side upper supporting element and the at least one body-side lower supporting element.

7. A surgical apparatus in accordance with claim 1, wherein the coupling device comprises a first coupling element for the at least one introduction-side upper supporting element and a first coupling element for the at least one introduction-side lower supporting element which, in the introduction position of the implant, are spread further relative to each other along the spreading direction by means of the fixing device than in the basic position of the implant.

8. A surgical apparatus in accordance claim 1, wherein the at least one first coupling element is formed as a first carrier which comprises at a free end the introduction-side supporting element and forms a slide-on element which acts along the spreading direction for the at least one second coupling element, and wherein the at least one second coupling element is formed as a second carrier which comprises at a free end the body-side supporting element and forms a slide-on element which acts along the spreading direction for the at least one first coupling element.

9. A surgical apparatus in accordance with claim 1, wherein the fixing device has a substantially U-shaped cross section.

10. A surgical apparatus in accordance with claim 9, wherein the fixing device comprises a first segment and a second segment which respectively form an arm of the U and also a third segment which connects the first and the second segment at one of their respective ends.

11. A surgical apparatus in accordance with claim 10, wherein the first segment comprises or forms at a free end thereof remote from the third segment at least one first upper stop for the at least one introduction-side upper supporting element or a carrier incorporating it which acts in a direction opposed to the spreading direction and/or wherein the second segment comprises or forms at a free end thereof remote from the third segment at least one first lower stop for the at least one introduction-side lower supporting element or a carrier incorporating it which acts in a direction opposed to the spreading direction.

12. A surgical apparatus in accordance with claim 10, wherein the first segment comprises or forms at a free end thereof remote from the third segment at least one second upper stop for the at least one introduction-side upper supporting element or a carrier incorporating it which acts in the spreading direction and/or wherein the second segment comprises or forms at a free end thereof remote from the third segment at least one second lower stop for the at least one introduction-side lower supporting element or a carrier incorporating it which acts in the spreading direction.

13. A surgical apparatus in accordance with claim 10, wherein a first receptacle for an implant component is formed on the third segment, into which said receptacle the implant component is at least partly insertable for holding the fixing device on the implant.

14. A surgical apparatus in accordance with claim 13, wherein the first implant component is partly insertable into the first receptacle.

15. A surgical apparatus in accordance with claim 13, wherein a second receptacle is formed between the first segment and the second segment, in which said receptacle the other respective implant component is arranged when the fixing device is held on the implant.

16. A surgical apparatus in accordance with claim 1, wherein the fixing device is formed in one piece manner.

17. A surgical apparatus in accordance with claim 1, wherein the fixing device is made from a deformable material.

18. A surgical apparatus in accordance with claim 1, wherein the fixing device is pre-mounted on the implant.

19. A surgical apparatus in accordance with claim 1, wherein a fixing device mounted on the implant is releasable therefrom.

20. A surgical apparatus in accordance with claim 1, wherein the fixing device forms a first extraction bearing element for extracting the fixing device from the implant.

21. A surgical apparatus in accordance with claim 20, wherein the fixing device comprises or forms at least one extraction stop element which acts in an extraction direction that is oriented transversely relative to the clamping direction, wherein the extraction direction is oriented transversely relative to the spreading direction.

22. A surgical apparatus in accordance with claim 1, wherein the fixing device forms a first spreading bearing element for transferring the implant from the introduction position into the spread position.

23. A surgical apparatus in accordance with claim 22, wherein the fixing device comprises or forms at least one spreading stop element which acts along the clamping direction, wherein the at least one spreading stop element is coupled to a receptacle formed by the fixing device, in which said receptacle the first implant component is held.

24. A surgical apparatus comprising an implant for mutually supporting an upper spinous process of a first vertebral body by means of an upper supporting surface and a lower spinous process of a second vertebral body by means of a lower supporting surface,
wherein the implant comprises a first implant component and a second implant component which is configured such as to be movable relative thereto along a clamping direction in order to transfer the implant out of a basic position in a spreading direction that is oriented transversely relative to the clamping direction into a spread position in which the upper supporting surface and the lower supporting surface are a greater spacing from each other than in the basic position,
and wherein the implant comprises at least one introduction-side upper supporting element and at least one introduction-side lower supporting element that are used for laterally supporting the upper spinous process and the lower spinous process on the introduction-side, respectively, in the spread position of the implant,
wherein the apparatus comprises a fixing device for the implant that is used for spreading the at least one introduction-side upper supporting element and the at least one introduction-side lower supporting element relative to each other along the spreading direction and by means of which fixing device the implant is movable from the basic position into an introduction position in which the at least one introduction-side upper supporting element and the at least one introduction-side lower supporting element are at a greater spacing relative to each other than in the basic position, and from which the implant is transferable into the spread position by moving the second implant component relative to the first implant component along the clamping direction,
wherein the fixing device has a substantially U-shaped cross section.

25. A surgical apparatus comprising an implant for mutually supporting an upper spinous process of a first vertebral body by means of an upper supporting surface and a lower spinous process of a second vertebral body by means of a lower supporting surface,
wherein the implant comprises a first implant component and a second implant component which is configured such as to be movable relative thereto along a clamping direction in order to transfer the implant out of a basic position in a spreading direction that is oriented transversely relative to the clamping direction into a spread position in which the upper supporting surface and the lower supporting surface are a greater spacing from each other than in the basic position,
and wherein the implant comprises at least one introduction-side upper supporting element and at least one introduction-side lower supporting element that are used for laterally supporting the upper spinous process and the lower spinous process on the introduction-side, respectively, in the spread position of the implant,
wherein the apparatus comprises a fixing device for the implant that is used for spreading the at least one introduction-side upper supporting element and the at least one introduction-side lower supporting element relative to each other along the spreading direction and by means of which fixing device the implant is movable from the basic position into an introduction position in which the at least one introduction-side upper supporting element and the at least one introduction-side lower supporting element are at a greater spacing relative to each other than in the basic position, and from which the implant is transferable into the spread position by moving the second implant component relative to the first implant component along the clamping direction,
wherein the fixing device forms a first spreading bearing element for transferring the implant from the introduction position into the spread position, and
wherein the fixing device comprises or forms at least one spreading stop element which acts along the clamping direction, wherein the at least one spreading stop element is coupled to a receptacle formed by the fixing device, in which said receptacle the first implant component is held.

* * * * *